US008641670B2

(12) United States Patent
Yodfat et al.

(10) Patent No.: US 8,641,670 B2
(45) Date of Patent: Feb. 4, 2014

(54) PORTABLE INFUSION DEVICE WITH MEANS FOR MONITORING AND CONTROLLING FLUID DELIVERY

(75) Inventors: Ofer Yodfat, Maccabim-Reut (IL); Iddo M. Gescheit, Tel Aviv (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

(21) Appl. No.: 12/452,927

(22) PCT Filed: Jul. 31, 2008

(86) PCT No.: PCT/IL2008/001057
§ 371 (c)(1),
(2), (4) Date: Jan. 29, 2010

(87) PCT Pub. No.: WO2009/016636
PCT Pub. Date: Feb. 5, 2009

(65) Prior Publication Data
US 2010/0145276 A1 Jun. 10, 2010

Related U.S. Application Data

(60) Provisional application No. 60/963,148, filed on Aug. 1, 2007, provisional application No. 61/004,019, filed on Nov. 21, 2007.

(51) Int. Cl.
*A61M 1/00* (2006.01)
*A61M 37/00* (2006.01)

(52) U.S. Cl.
USPC ............... 604/151; 604/131; 604/65; 604/67

(58) Field of Classification Search
USPC ........ 604/65–67, 131, 19, 151; 600/365, 316, 600/347
See application file for complete search history.

(56) References Cited

U.S. PATENT DOCUMENTS 3,771,694 A 11/1973 Kaminski
4,498,843 A 2/1985 Schneider et al.
(Continued)

FOREIGN PATENT DOCUMENTS

EP 0399119 A1 11/1990
WO WO-03026726 A1 4/2003
(Continued)

OTHER PUBLICATIONS

Boizel, R., "Glucose monitoring and pump data management software operated on a personal digital assistant can contribute to improve diabetes control in CSII-treated patients", *Diabetes Metab.*, 33:314-315 (2007).

(Continued)

*Primary Examiner* — Quynh-Nhu H Vu
(74) *Attorney, Agent, or Firm* — Mintz Levin Cohn Ferris Glovsky and Popeo, P.C.

(57) ABSTRACT

A device (1000) for delivering a therapeutic fluid (e.g. insulin) into a body of a patient are provided. In one aspect, the device can be implemented with a help of a patch unit (10) securable to a cradle unit (20) or to the body of the patient. The patch unit can employ a driving mechanism (120), a power source (210), a processor (110), a user interface (14) and a display(12). The processor can be adapted for controlling the driving mechanism by using one or more inputs. The inputs can corresponding to a basal rate and/or a bolus profile. The display can be adapted for displaying the inputs. The user interface can be adapted for adjusting the inputs.

51 Claims, 40 Drawing Sheets

(56) References Cited

U.S. PATENT DOCUMENTS

| | | | |
|---|---|---|---|
| 4,657,486 A | 4/1987 | Stempfle et al. | |
| 5,507,288 A * | 4/1996 | Bocker et al. | 600/322 |
| 5,820,622 A * | 10/1998 | Gross et al. | 604/890.1 |
| 5,957,895 A | 9/1999 | Sage et al. | |
| 5,984,894 A * | 11/1999 | Poulsen et al. | 604/151 |
| 6,024,539 A * | 2/2000 | Blomquist | 417/63 |
| 6,485,461 B1 | 11/2002 | Mason et al. | |
| 6,589,229 B1 | 7/2003 | Connelly et al. | |
| 6,659,978 B1 | 12/2003 | Kasuga et al. | |
| 6,723,072 B2 | 4/2004 | Flaherty et al. | |
| 6,740,059 B2 | 5/2004 | Flaherty | |
| 6,749,587 B2 * | 6/2004 | Flaherty | 604/151 |
| 7,232,423 B2 * | 6/2007 | Mernoe | 604/135 |
| 7,922,708 B2 * | 4/2011 | Estes et al. | 604/500 |
| 2003/0065308 A1 * | 4/2003 | Lebel et al. | 604/891.1 |
| 2003/0212364 A1 * | 11/2003 | Mann et al. | 604/131 |
| 2005/0215982 A1 * | 9/2005 | Malave et al. | 604/890.1 |
| 2007/0106218 A1 * | 5/2007 | Yodfat et al. | 604/131 |
| 2007/0191702 A1 | 8/2007 | Yodfat et al. | |
| 2008/0077081 A1 * | 3/2008 | Mounce et al. | 604/67 |
| 2008/0319414 A1 | 12/2008 | Yodfat et al. | |
| 2008/0319416 A1 | 12/2008 | Yodfat et al. | |
| 2010/0137790 A1 | 6/2010 | Yodfat | |
| 2010/0204657 A1 | 8/2010 | Yodfat et al. | |

FOREIGN PATENT DOCUMENTS

| | | |
|---|---|---|
| WO | WO-2006121921 A2 | 11/2006 |
| WO | WO-2008020447 A1 | 2/2008 |
| WO | WO-2008078318 A2 | 7/2008 |
| WO | WO-2008122983 A1 | 10/2008 |

OTHER PUBLICATIONS

Hoogma et al., "Comparison of the effects of continuous subcutaneous insulin infusion (CSII) and NPH-based multiple daily insulin injections (MDI) on glycaemic control and quality of life: results of the 5-nations trial", *Diabetes Med.*, 23(2):141-147 (2007).

International Search Report for PCT Application No. PCT/IL2008/001057, mailed Jan. 29, 2009.

Parkner et al., "Overnight CSII as supplement to oral antidiabetic drugs in Type 2 diabetes", *Diabetes Obes. Metab.*, 10:556-563 (2007).

Written Opinion of the International Search Authority for PCT Application No. PCT/IL2008/001057, mailed Jan. 29, 2009.

\* cited by examiner

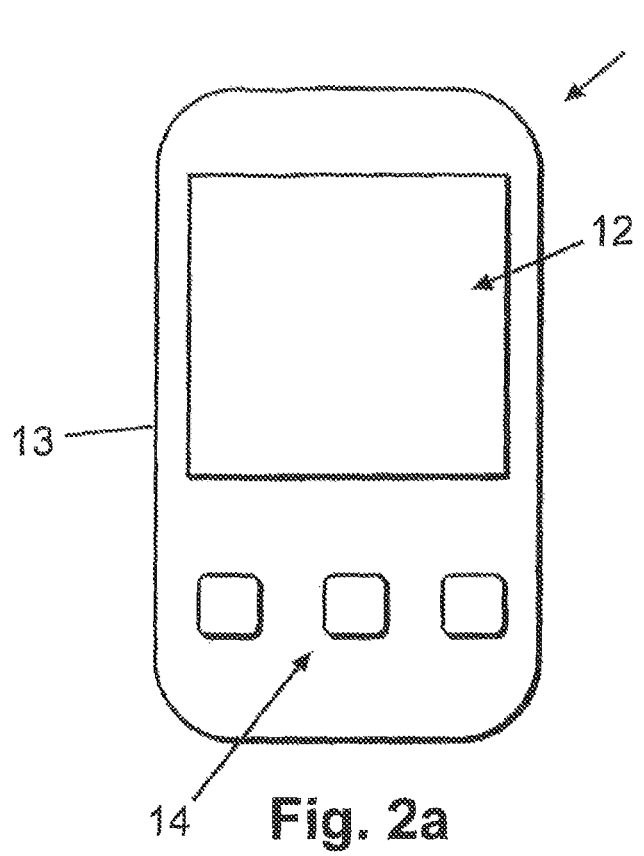
Fig. 2a
Fig. 2b
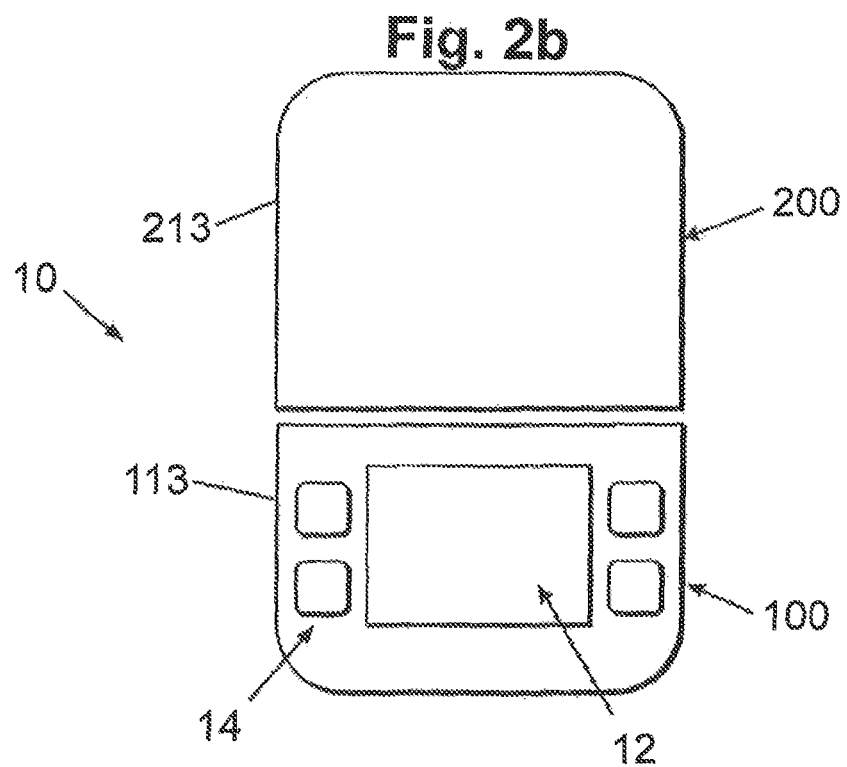

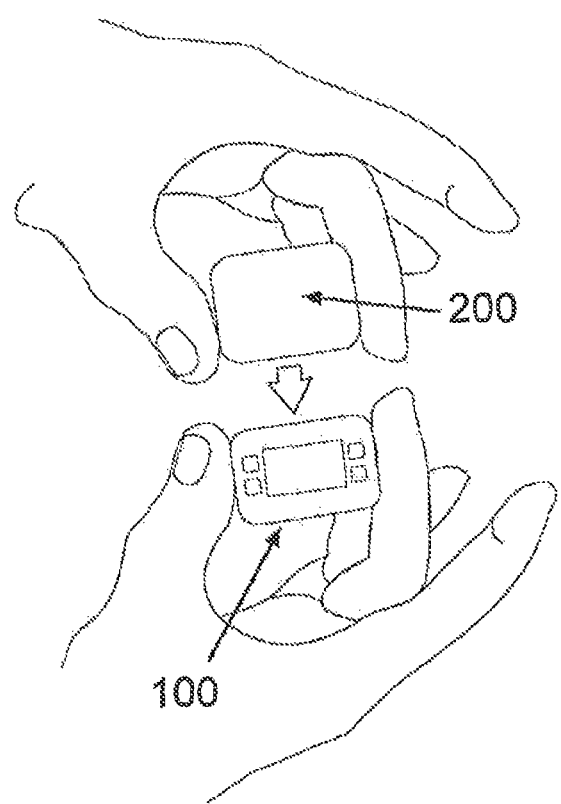
Fig. 5a
Fig. 5b
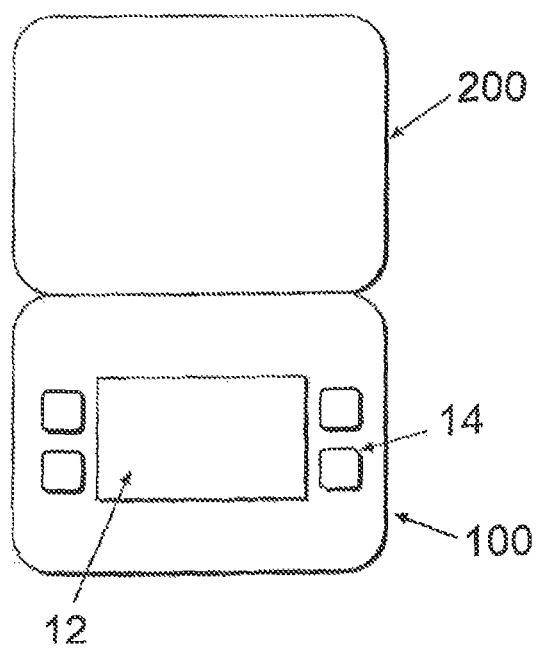

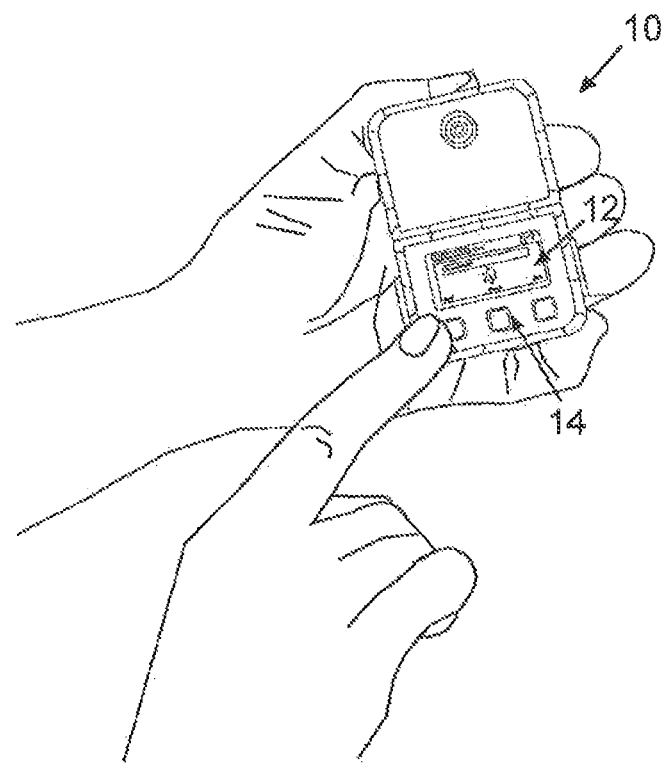
Fig. 13k
Fig. 13l
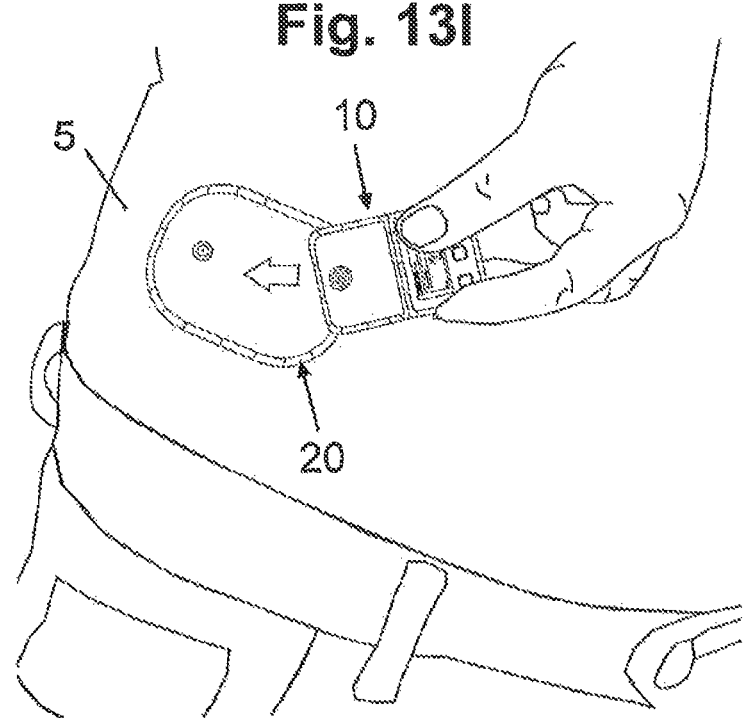

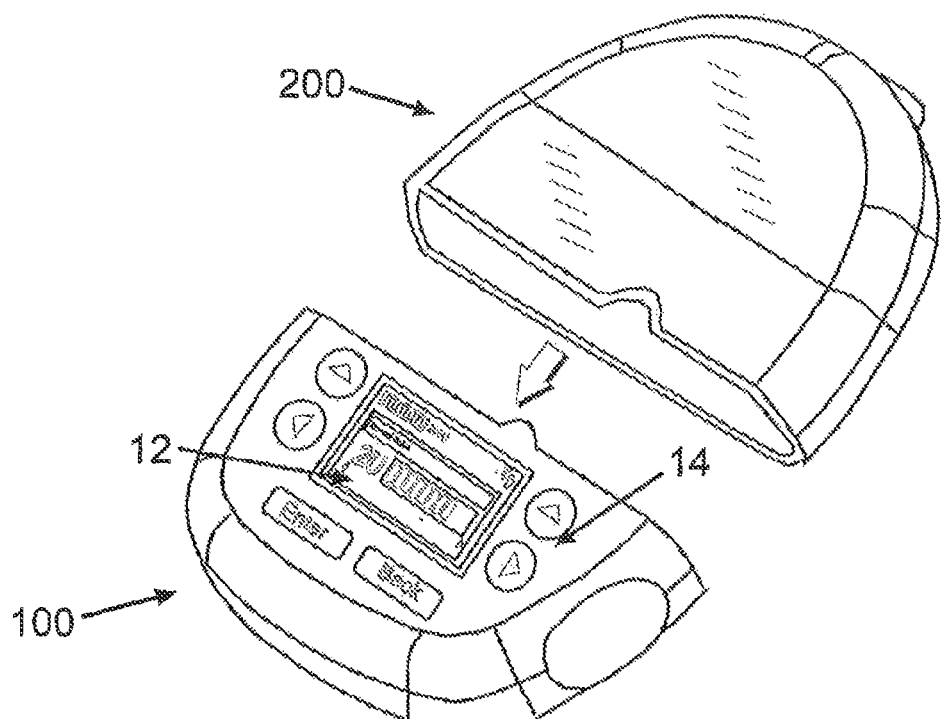
Fig. 14a
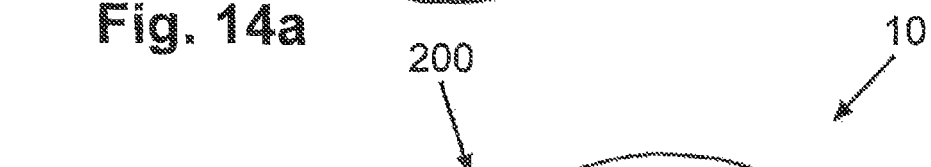
Fig. 14b
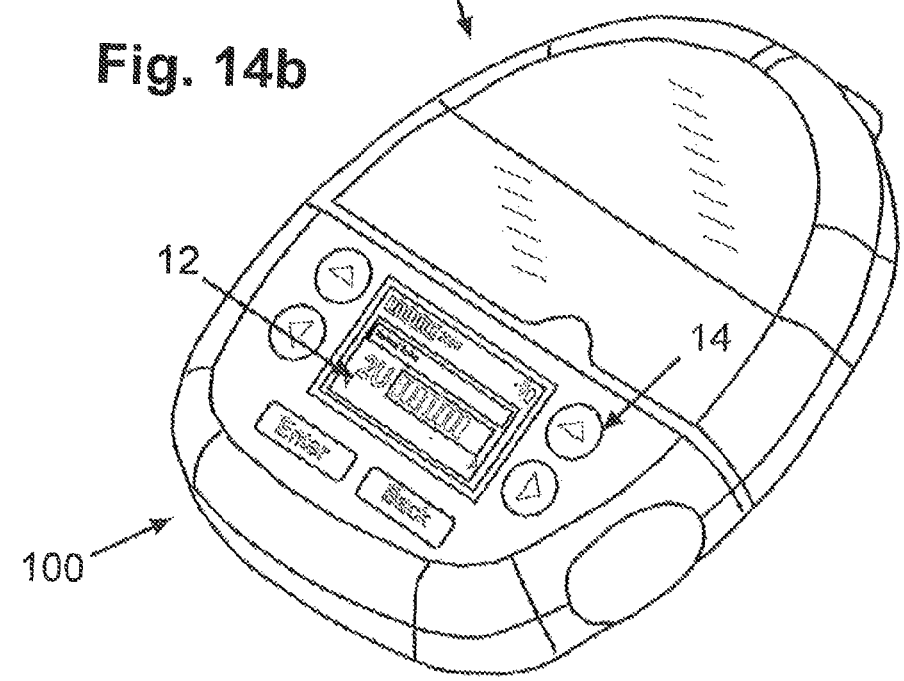

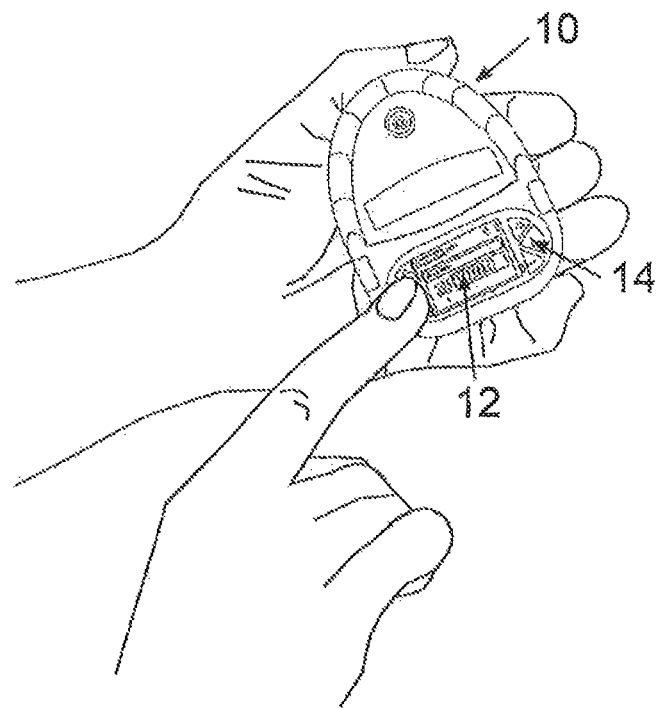
Fig. 20e
Fig. 20f
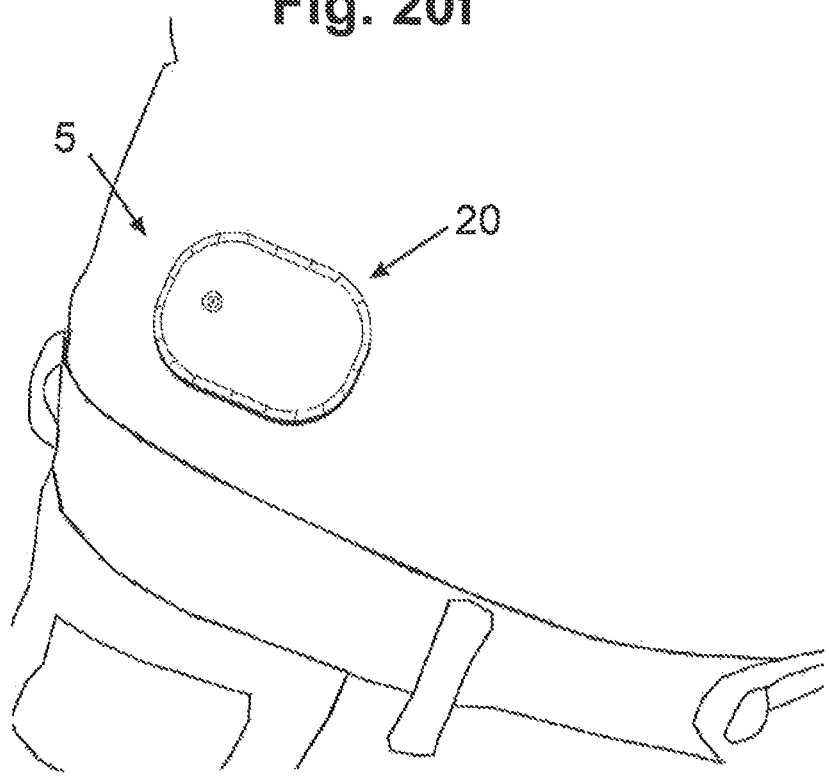

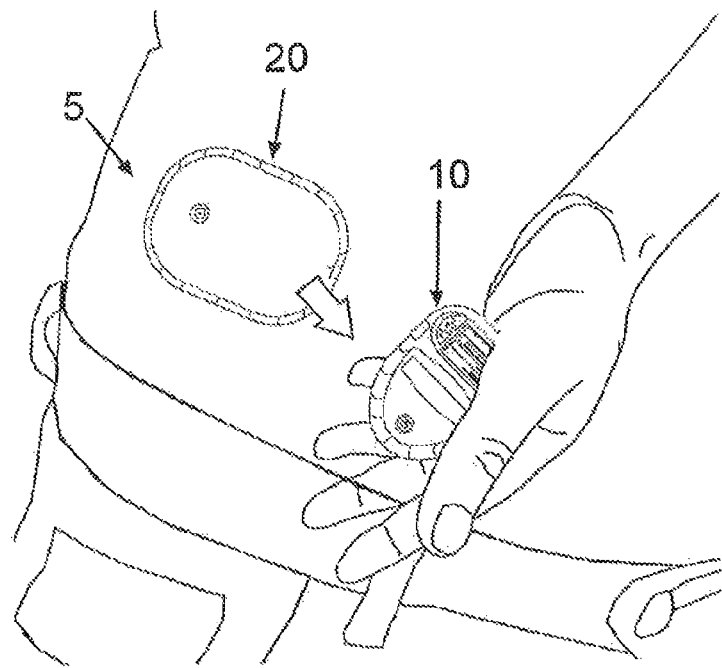
Fig. 20i
Fig. 20j
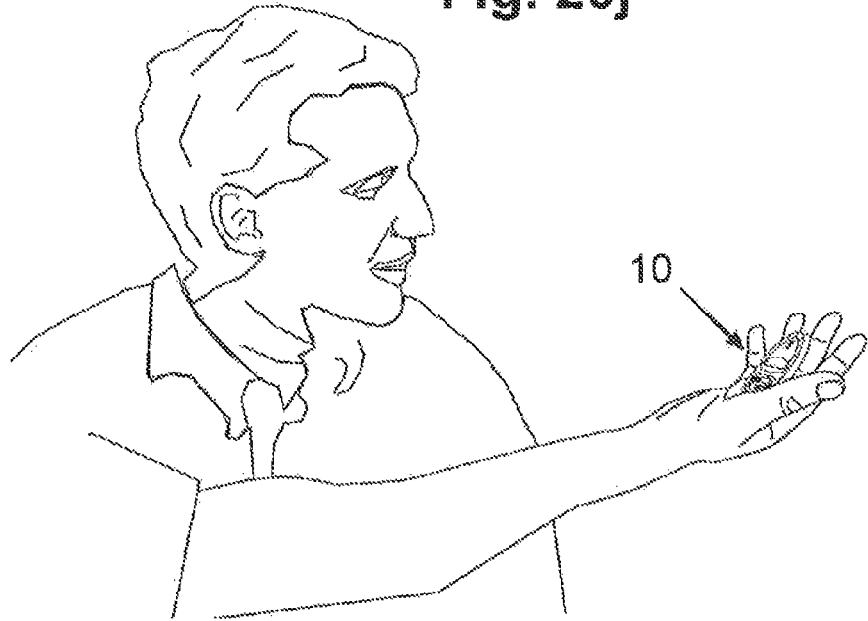

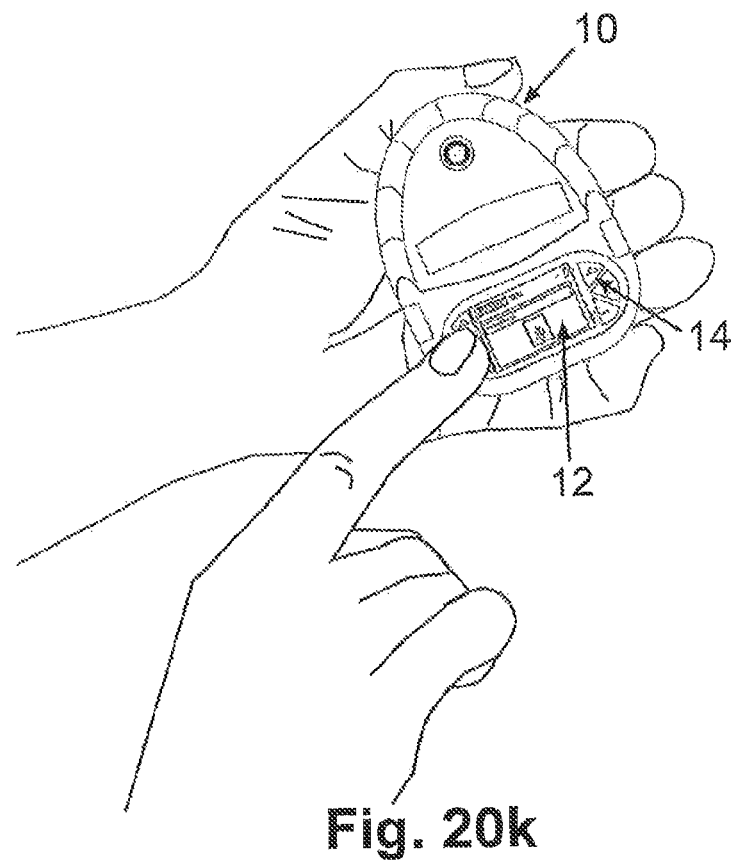
Fig. 20k
Fig. 20l
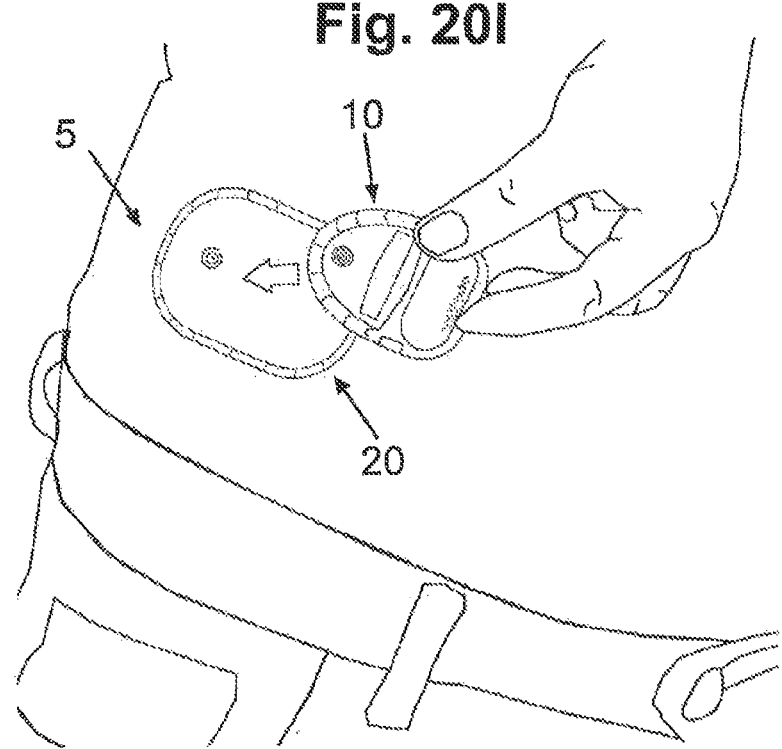

PORTABLE INFUSION DEVICE WITH MEANS FOR MONITORING AND CONTROLLING FLUID DELIVERY

CROSS-REFERENCE TO RELATED APPLICATIONS

The present application is a 35 U.S.C. §371 national stage entry of PCT/IL2008/001057, which has an international filing date of 31 Jul. 2008 and claims priority to U.S. Provisional Patent Application Nos. 60/963,148, filed on 1 Aug. 2007 and 61/004,019, filed on 21 Nov. 2007. The present application incorporates herein by reference the disclosure of each of the above-referenced applications in its entirety.

FIELD OF THE INVENTION

A system, a device and a method for sustained medical infusion of fluids are described. In some implementations the described device can include a miniature portable infusion unit that can be attachable to a patient's body. The device can include a skin-adherable dispensing unit/device that can periodically be disconnected from and reconnected to the body. The described device can be disconnected and reconnected to the body and can be provided with means for monitoring and controlling the fluid delivery.

BACKGROUND OF THE INVENTION

Medical treatment of several illnesses requires continuous drug infusion into various body compartments, such as subcutaneous and intra-venous injections. Diabetes mellitus (DM) patients, for example, require the administration of varying amounts of insulin throughout the day to control their blood glucose levels. In recent years, ambulatory portable insulin infusion pumps have emerged as a superior alternative to multiple daily syringe injections of insulin, initially for Type 1 diabetes patients (Diabetes Medicine 2006; 23(2): 141-7) and consecutively for Type 2 (Diabetes Metab Apr. 30, 2007 Diabetes Obes Metab Jun. 26, 2007). These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to individual prescription, since an overdose or under-dose of insulin could be fatal.

The first generation of portable infusion pumps concerns "pager-like" devices with a reservoir contained within the device's housing. A long tube delivers insulin from the pump attached to a patient's belt to a remote insertion site. Both basal and bolus volumes deliveries in these "pager-like" devices are controlled via a set of buttons provided on the device. A screen/display is provided on the device housing providing the user with fluid delivery status, programming flow delivery, alerts and alarms. Such devices are disclosed, for example, in U.S. Pat. Nos. 3,771,694, 4,657,486 and 4,498,843. These devices represent a significant improvement over multiple daily injections, but nevertheless, they all suffer from several major drawbacks, among which are the large size and weight, long tubing and lack of discreetness.

To avoid the consequences of long delivery tube, a new concept on which a second generation pumps are based, was proposed. As described in prior art, the new concept concerns a remote controlled skin adherable device with a housing having a bottom surface adapted for contact with the patient's skin, a reservoir disposed within the housing, and an injection needle adapted for communication with the reservoir. The user interface means can be represented by a remote controller that contains operating buttons and screen/display providing fluid delivery status, programming flow delivery, alerts and alarms. This paradigm was described, for example, in U.S. Pat. Nos. 5,957,895, 6,589,229, 6,740,059, 6,723,072 and 6,485,461.

These second generation devices also have several limitations; they are heavy and bulky, not detachable, and expensive because the entire device should be discarded every 2-3 days. Another major drawback of these 2nd generation skin adherable devices concerns the remote controlled drug administration. The user is totally dependent on the remote control and cannot initiate bolus delivery or operate the device if the remote control is not at hand, lost or has malfunctioned (practically, the patient cannot eat).

A third generation of skin adherable infusion devices was devised to avoid the price limitation and to extend patient customization. An example of such a device was described in our previous patent applications U.S. Ser. No. 11/397,115 and PCT/IL06/001276. This third generation device contains a remote control unit and a skin adherable patch unit (also referred to as "dispensing patch unit") that can be comprised of a reusable part and a disposable part. The reusable part can contain the metering portion, electronics, and other relatively expensive components. The disposable part can contain the reservoir and in some embodiments batteries. A tube can deliver the fluid from the reservoir to an exit port that contains a connecting lumen. This concept provides a cost-effective skin adherable infusion device and allows diverse usage such as various reservoir sizes, various needle and cannula types, etc.

Generally, the skin adherable infusion devices of third generation require a remote control. The remote control can be carried out by a remote control unit, which is a separate item. In addition to the disadvantage of being bulky and heavy, the remote control unit can be easily lost and it is one of the greatest fears of diabetic patients to loose the remote control unit, since in this situation the patient can not operate the pump to dispense insulin into the body. In extreme situations, losing the remote control unit could have serious consequences for the patient's health. It is worth mentioning that skin adherable patches are known already for a relatively long time and therefore, the above-mentioned problem associated with a separate remote control unit is not new. Nevertheless, it only recently has been suggested to provide an adherable patch with a possibility for autonomous control instead of or in addition to remote control. The autonomous control is achieved by providing the patch with dedicated operating buttons/switches which allow operating the patch and thus, eliminating the necessity in separate remote control unit.

In our U.S. Provisional Patent Application No. 60/876,679, a 4th generation patch/device unit has been disclosed. The $4^{th}$ generation unit can be disconnected and reconnected to the body by virtue of a skin adherable cradle unit. After reservoir filling, the process of mounting the patch unit to the patient generally includes attaching the cradle unit the skin of the patient, inserting a cannula through a cradle opening (a "well") into the subcutaneous tissue, and connection of the patch unit to the cradle unit.

The 4th generation detachable skin adherable patch can be either remotely controlled or operated by a dedicated control button(s)/switch(es) that are located on the patch housing (preferably on the reusable part) as disclosed in our co-pending U.S. Provisional Patent Application No. 60/691,527, filed Jul. 20, 2007, and titled "Manually Operable Portable Infusion Pump". By virtue of the 4th generation patch device, the user can deliver a desired bolus dose by repetitive pressing of control buttons ("Bolus buttons") and the separate remote control unit is not any more necessary.

The co-pending U.S. patent application Ser. No. 11/706, 606 discloses a dual function dispensing device that contains a dispensing patch/device unit (i.e. insulin dispensing patch) and an analyte sensing means (i.e. continuous glucose monitor). This dual function device can have the same configuration that was outlined above and can also be disconnected from and reconnected to the body at patient discretion.

The patch unit of the 4$^{th}$ generation devices does not have a screen or a display. Thus, without the remote control, the patient may not be aware of the current state of the system (real time and/or historical data). The two operating buttons/switches provided at the patch unit cannot be used for other functions. For example, configuration the operating buttons cannot be used to configure a basal rate or a bolus profile.

BRIEF DESCRIPTION OF DRAWINGS

FIG. 2a shows one implementation of a one-part patch unit.

FIG. 2b shows one implementation of a two-part patch unit comprising a reusable part and disposable part.

FIGS. 4 and 5 show some implementations of the two part patch unit and various options for connecting the reusable part and the disposable part.

FIG. 14 shows an isometric view of one implementation of the two part patch unit before and after connection.

SUMMARY OF THE INVENTION

Figure 1:
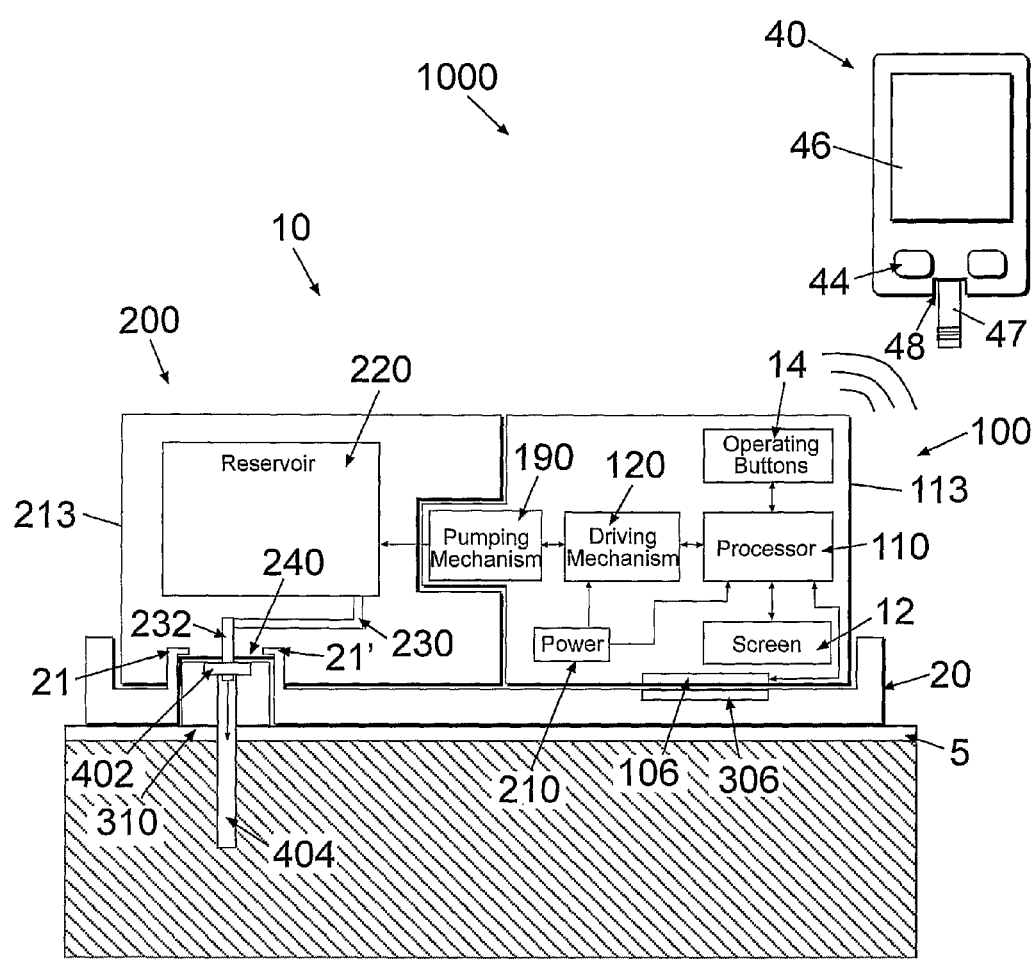
FIG. 1 shows a general view of the device and its components.

A device and a method for delivering a therapeutic fluid (e.g. insulin) into a body of a patient are provided. In one aspect, the device can be implemented with a help of a patch unit securable to a cradle unit or to the body of the patient. The patch unit can employ a driving mechanism, a power source, a processor, a user interface and a display. The processor can be adapted for controlling the driving mechanism by using one or more inputs. Some of the inputs can be corresponding to a basal rate and/or a bolus profile. The display can be adapted for displaying the inputs. The user interface can be adapted for adjusting the inputs.

In one variation, the display can be coverable by a flip. The display can also be touch sensitive. The patch unit can have a disposable part and a reusable part. The reusable part can employ the driving mechanism, the processor, the user interface and the display. The disposable part can employ the power source and a reservoir adapted for storing the therapeutic fluid.

In one implementation, the disposable part and the reusable part can be secured in a side by side configuration. In another implementation, the disposable part and the reusable part are secured in a sandwich configuration. The disposable part can be securable to the reusable part by using a sealing means. The disposable part can have a port for attachment of a vial. The cradle can have a well for insertion of a cannula. The patch unit can be remotely controlled. The patch unit can also be provided with at least one manual control button.

The processor can control the patch unit based on a position indication signal received from a position detector. The processor can also control the delivery of the therapeutic fluid into the body of the patient based on a position indication signal received from a position detector. The processor can be configured to initiate a notification to the patient.

The cradle unit can have a cradle base portion. The cradle base portion can be a flat sheet with an adhesive layer facing a skin of the patient and having anchoring means for connection and disconnection of said patch unit. The cradle unit can also have a well configured to protrude upwardly from the cradle base. The well can be adapted for insertion of a cannula into the body of the patient. The patch unit can also employ a peristaltic mechanism for delivering the therapeutic fluid into the body of the patient. The patch unit can employ a piston for delivering the therapeutic fluid into the body of the patient. In some implementations, for delivering a therapeutic fluid can include an apparatus for sensing a bodily analyte level. For example, the bodily analyte can be glucose.

The display can be adapted to display additional data related to diabetes treatment such as, for example, blood glucose level, nutrition values of foods (e.g. amount of carbohydrates), amount of therapeutic fluid held in the patch unit, amounts and/or percentages of delivered therapeutic fluid.

In another aspect, the method for delivering a therapeutic fluid into a body of a patient using a therapeutic fluid delivery device can be implemented by receiving one or more inputs from a user interface, wherein the inputs correspond to a basal rate and/or a bolus profile. The method can also be implemented by displaying the inputs on a display of the patch unit, wherein the patch unit is securable to a cradle unit or to the body of the patient, and wherein the patch unit employs a driving mechanism, a power source, a processor, a user interface and the display. The method can also be implemented by controlling the driving mechanism operating within a patch unit by using the received inputs.

DETAILED DESCRIPTION OF THE PREFERRED EMBODIMENTS

FIG. 1 illustrates a device (1000) that can include portable infusion means for continuous delivery of a therapeutic fluid(s) into the body (i.e. insulin). The device can be provided with a means for continuously monitoring bodily analyte level (i.e. glucose). The device (1000) can include one or more of the units. For example, the device (1000) can include a dispensing patch unit (10) (hereinafter "dispenser", "patch unit" "device" or "patch"). The patch can contain operating buttons/switches/keys (14) and a screen/display (12) for programming, controlling and indications of flow and of dispenser operation.

The patch unit can comprise a disposable part and a reusable part. The reusable part (100) in the housing (113) can contain the Printed Circuit Board (PCB)/processor (110), the driving mechanism (120), the pumping mechanism (190) and the power source (210). The housing (113) of the reusable part (100) can be provided with buttons (14) and display (12). A "position detector" (106) can be provided in the reusable part (100) for automatic flow suspension or resumption upon respective disconnection or reconnection of the dispensing unit (10).

The disposable part (200) in the housing (213) can contain the reservoir (220), the delivery tube (230), and the means for fluid communication of the reservoir (220) with the cannula (404), hereinafter referred-to as a "connecting lumen" (232). The connecting lumen is positionable within the outlet port (240).

In some implementations, the cradle unit (hereinafter "cradle") (20) can be adherable to patient skin (5). The cradle (2) can allow easy disconnection and reconnection of the patch (10) to and from the body. The cradle (20) can have an opening (310) to allow cannula (404) insertion through the cradle (20) into the body. The cradle can have a connecting means (i.e. latches) for patch (10) connection and disconnection. The cradle (20) can be provided with a notification means—referred-to further as "position sensor" (306) for automatic flow suspension or flow resumption upon disconnection and reconnection of the patch and cradle respectively.

In some implementations, the cannula (404) can be a soft tube inserted through the cradle (20) and patient's skin (5) with the aid of a penetrating member (not shown). During connection of patch (10) and cradle (20) the connecting lumen (232) pierces a rubber septum (402) provided at the upper end of the cannula and thus fluid communication can be established and maintained between reservoir (220) and body. The cannula (404) can be inserted manually or automatically with the aid of an inserter (not shown) through the opening (310) in the cradle into the body. After insertion, the cannula (404) can be secured to the cradle (20) by anchoring means (21 and 21'). The opening (310) to which the anchoring means (21 and 21') secure the cannula hereinafter will be referred-to as "well".

The Remote control (40) can contain operating buttons/switches/keys (44) and a display (46) for remote programming of flow instructions, data acquisition and presentation. In some implementations, the remote control (40) can contain a blood glucose monitoring apparatus, which can be provided with a glucose test strip (47) insertable into a slot (48) and with a display (46) for presentation of glucose readings. For example, the display (46) can be touch sensitive. Touch sensitive displays can work in place of or in addition to other buttons/switches/keys.

FIG. 2a shows a general view of a single part patch unit (10) of the device. The patch unit (10) can be provided with a housing (13), a display (12), and operation buttons (14).

FIG. 2b shows a general view of a two-part patch unit (10) of the device which can be composed of a disposable part (200) and a reusable part (100). The reusable part (100) can contain a housing (113), a display (12), and operation buttons (14). The disposable part (200) can contain a housing (213) in which resides a reservoir (not shown).

Figure 3A:
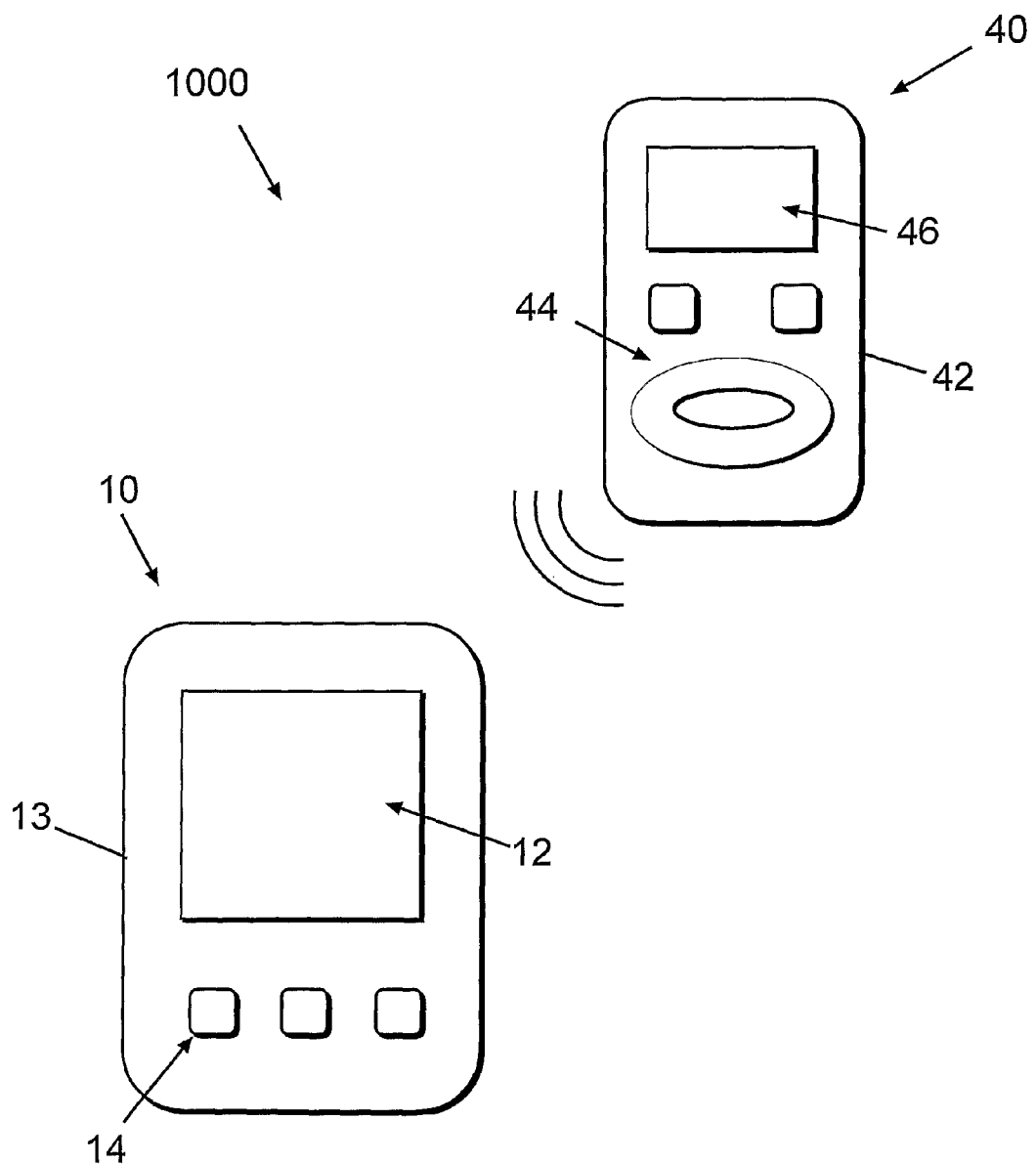
FIG. 3a shows one implementation of the device including a one-part patch unit and a remote control unit.
Figure 3B:
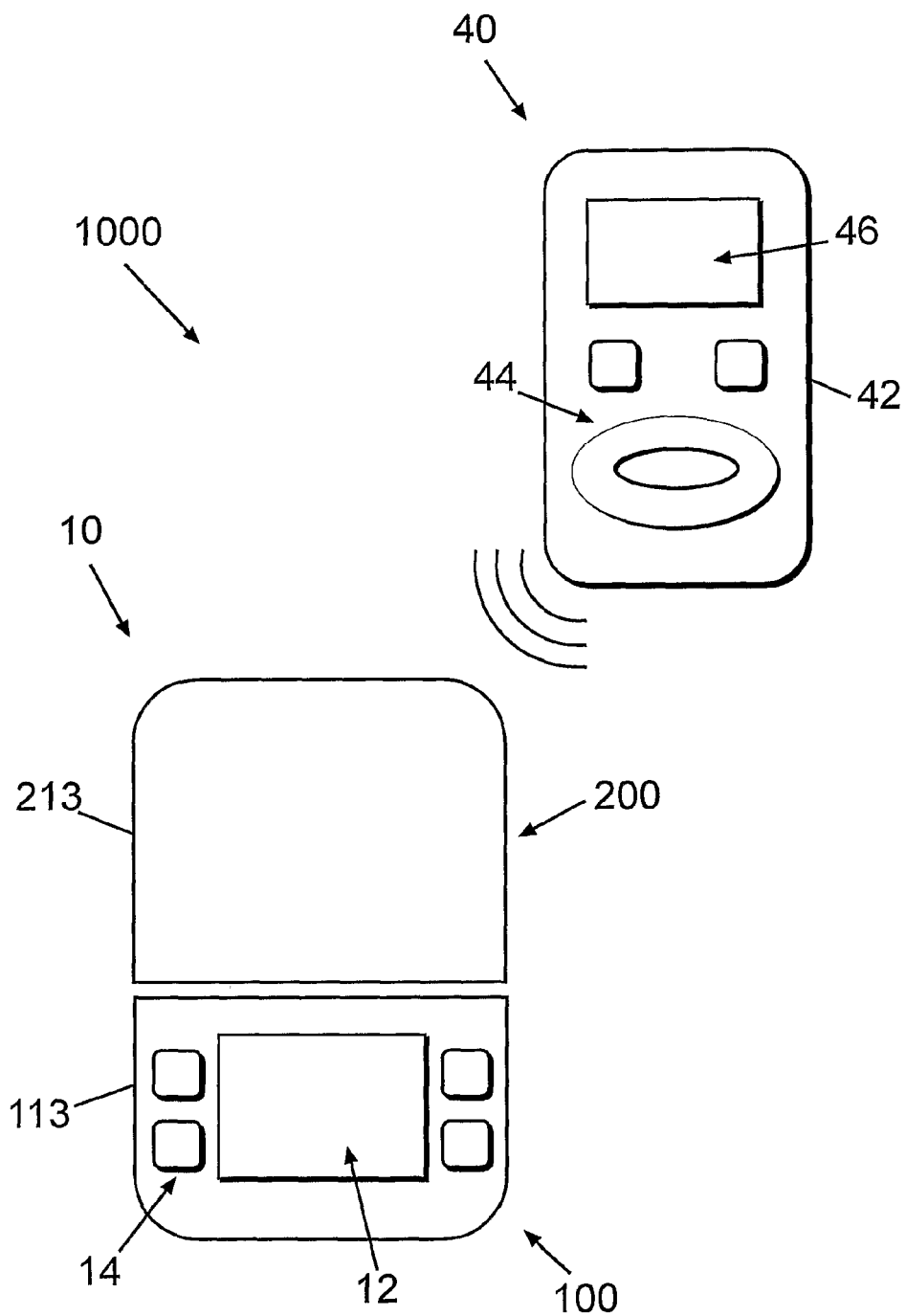
FIG. 3b shows one implementation of the device including a two-part patch unit and a remote control unit.
Figure 4A:
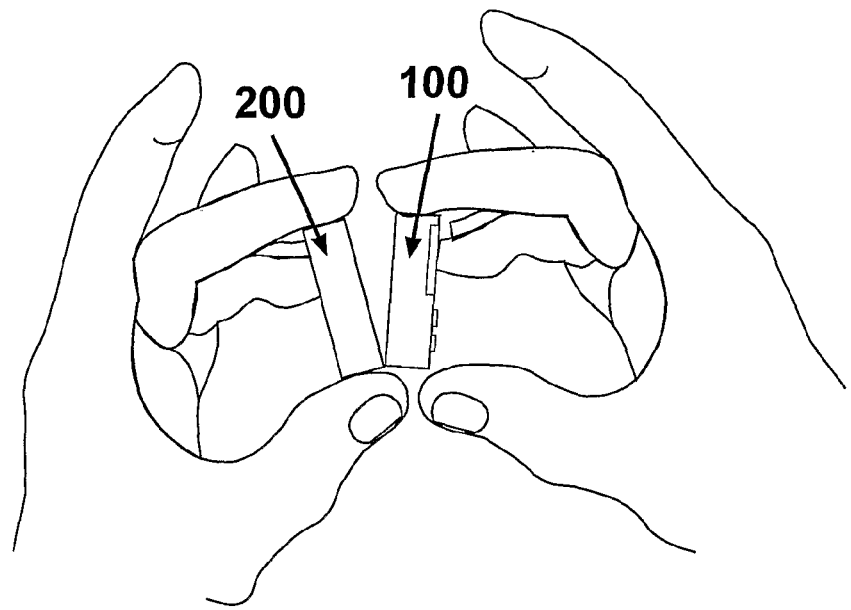
Figure 4B:
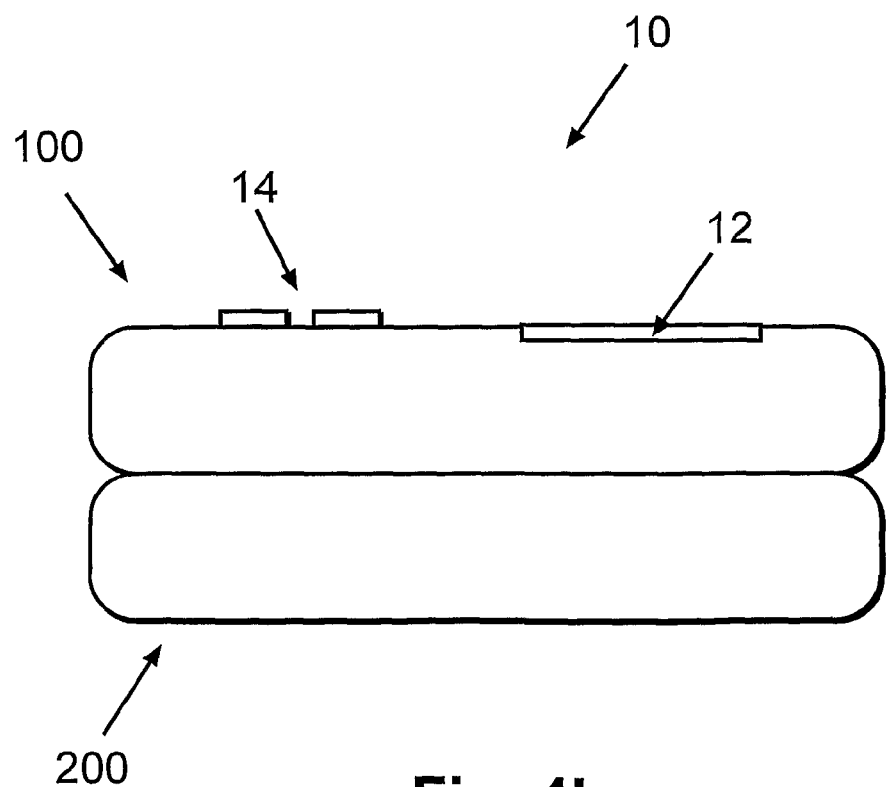
Figure 6A:
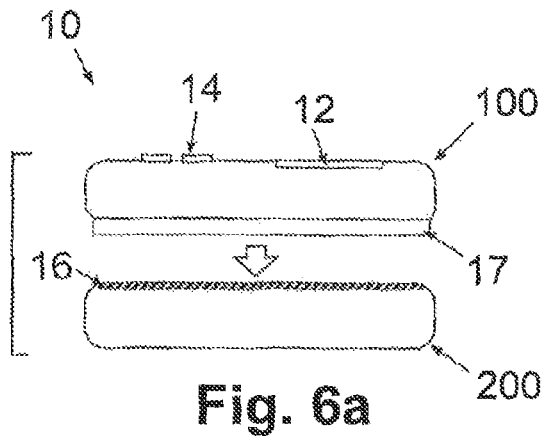
FIGS. 6 and 7 show some implementations of the two part patch unit and sealing solutions.
Figure 6B:
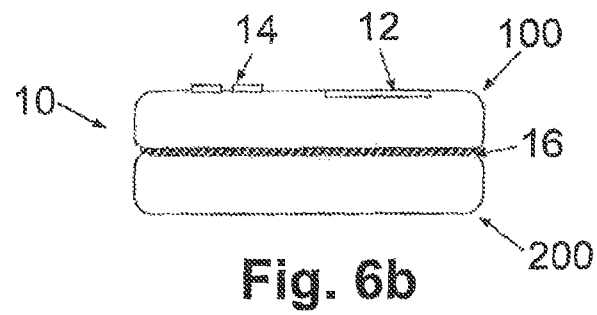
Figure 6C:
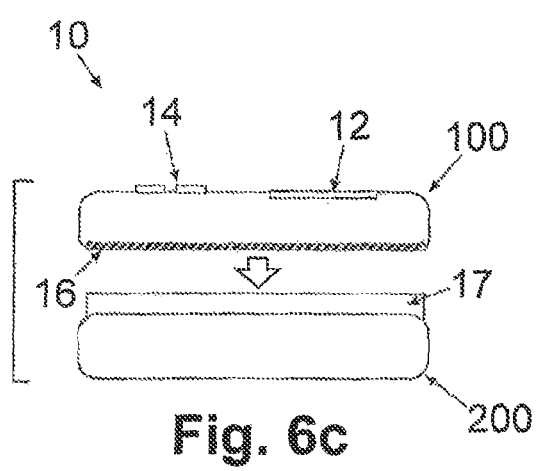
Figure 6D:
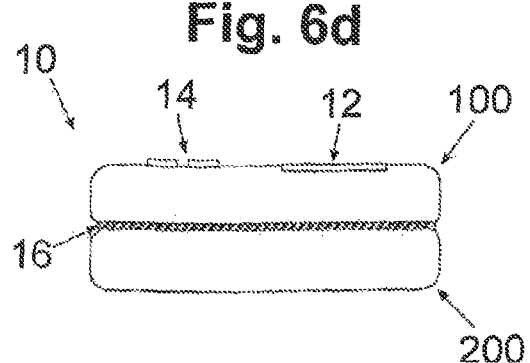

FIG. 3a shows the device (1000) that can be provided with a single part patch unit (10) and with a remote control unit (40). The patch unit (10) can contain a housing (13), operation buttons (14), and a display (12). The remote control unit (40) can contain a housing (42), operating buttons (44) and a display (46). The patch unit (10) can be operated and controlled with the use of buttons (14) and display (12) located on the patch housing (13) or alternatively with the use of the remote control unit (40). FIG. 3b shows a device (1000) that can be provided with a two-part patch unit (10) (reusable (100) and disposable (200)), and a remote control unit (40). The reusable part (100) can be operated and controlled with the aim of buttons (14) and a display (12) located on the housing (113) of the reusable part or alternatively by the remote control unit (40).

FIGS. 4-7 show some examples of connecting the reusable (100) and disposable (200) parts and means for securing the two after the connection. For example, FIG. 4a shows a back-to-back ("sandwich type") connection of the disposable part (200) and the reusable part (100). FIG. 4b shows the parts after connection. The reusable part (100) can be provided with operation buttons (14) and display (12).

FIG. 5a shows a face-to-face ("side by side") connection of the disposable part (200) and the reusable part (100). FIG. 5b shows the parts after connection. The reusable part (100) can be provided with operation buttons (14) and display (12).

FIGS. 6 and 7 show some examples of connecting the two parts of the patch unit (10) and the securing means (16) employed in a "sandwich type" and a "side by side" configurations respectively. FIG. 6a shows the reusable part (100) provided with a protrusion (17) and the disposable part (200) provided with the securing means (16). The securing means (16) can be configured as a seal. In some implementations, the securing means and/or the sealing means can be made of rubber, silicone or any other elastic material. The securing means can also be configured as a gasket (e.g. O-ring). The reusable part (100) and disposable part (200) are connected in a "sandwich type" configuration when the protrusion (17) of the reusable part (100) slides beneath and then inside the circumference of the securing means (16) of the disposable part (200). The securing means made of elastomer is squeezed between the two parts, covering and pressing the protrusion (17) and thus sealing the contact area between the two parts. In another implementation, the protrusion (17) can be provided on the disposable part (200) and the securing means (16) on the reusable part (100). FIG. 6b shows the two connected parts. FIG. 6c shows the patch unit (10) before parts connection. The protrusion (17) can be provided on the disposable part (200) and the securing means (16) on the reusable part (100). FIG. 6d shows the two connected parts.

Figure 7A:
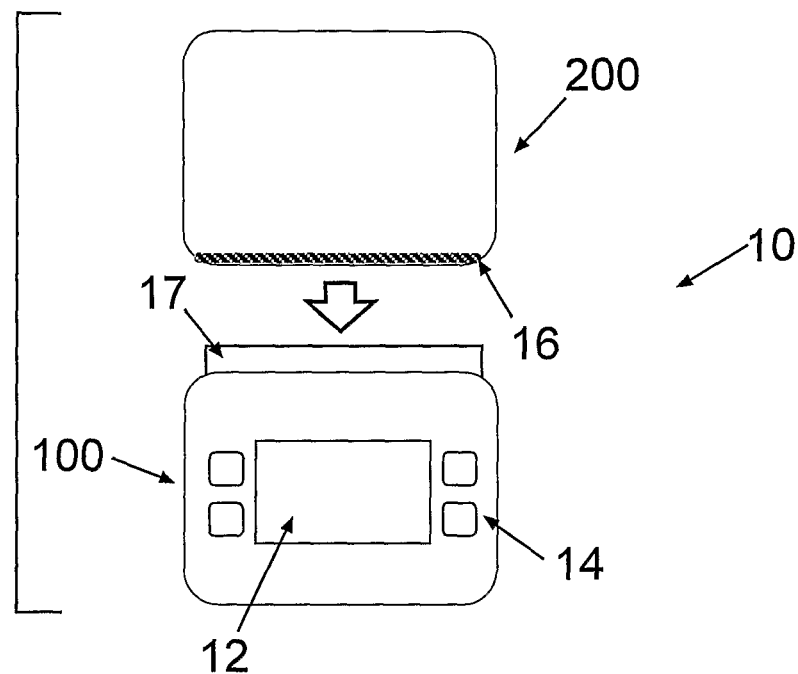
Figure 7B:
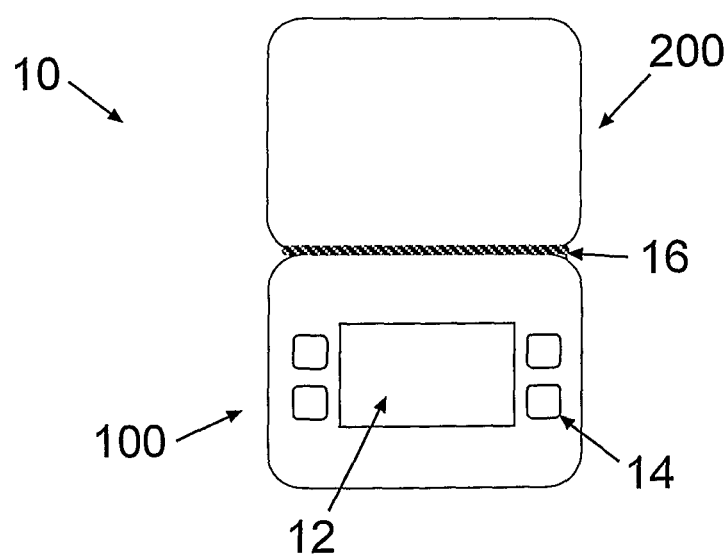
Figure 7C:
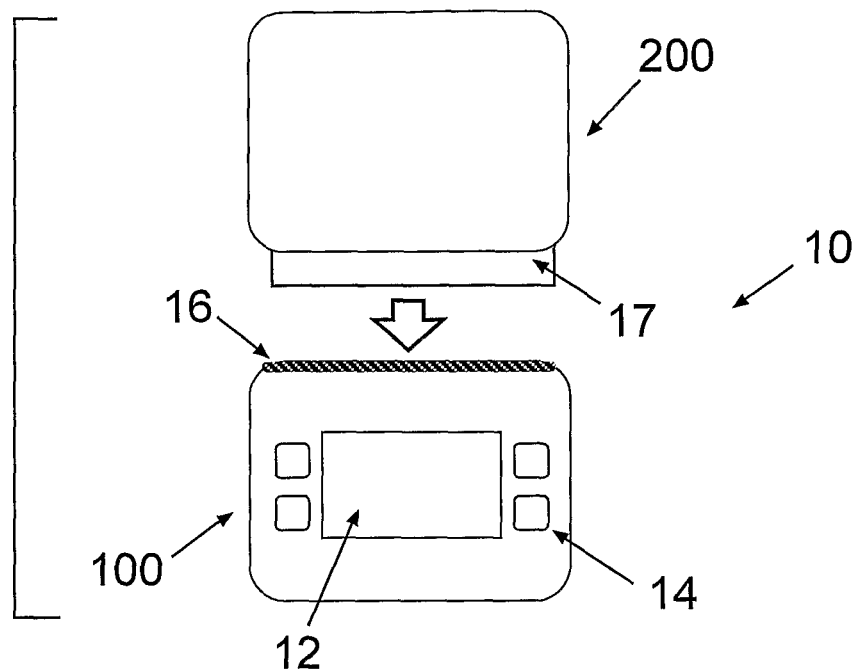
Figure 7D:
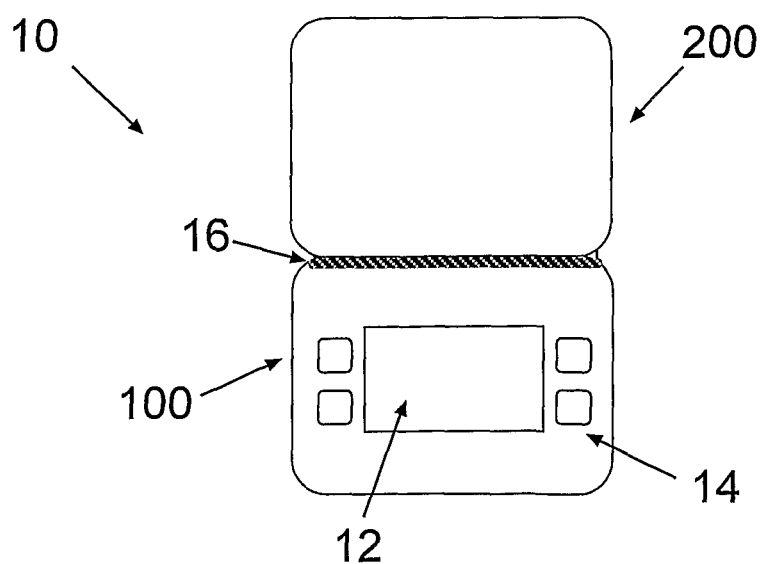
Figure 8A:
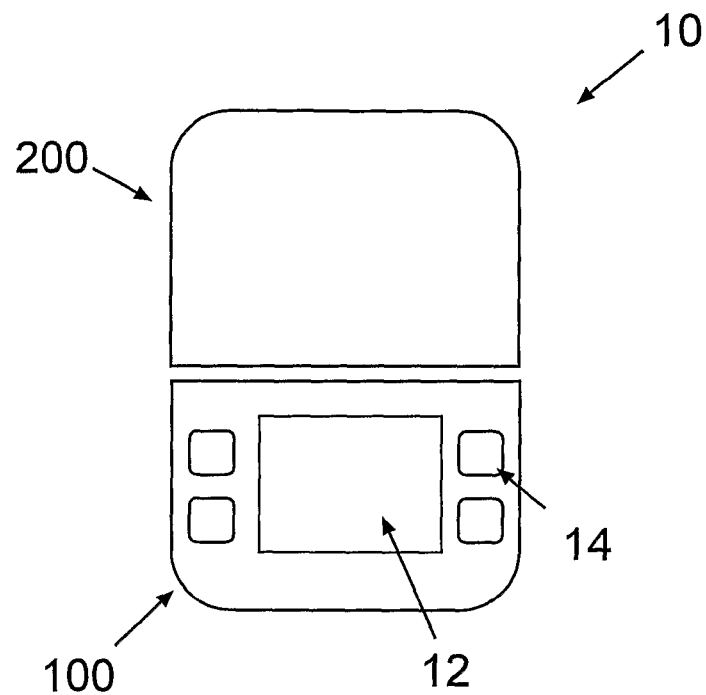
FIG. 8 shows one implementation of optional locations of the operating buttons and display on the patch unit.
Figure 8B:
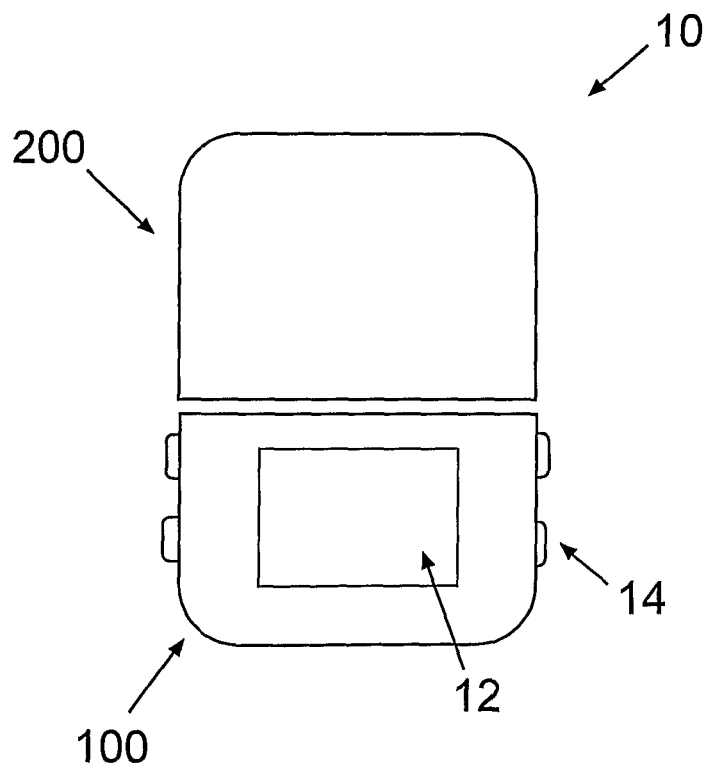
Figure 8C:
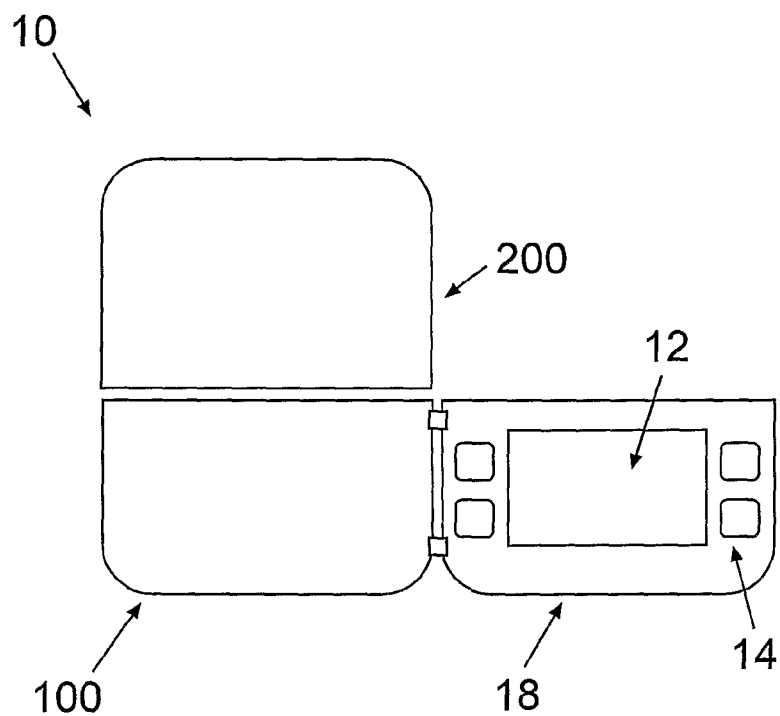
Figure 8D:
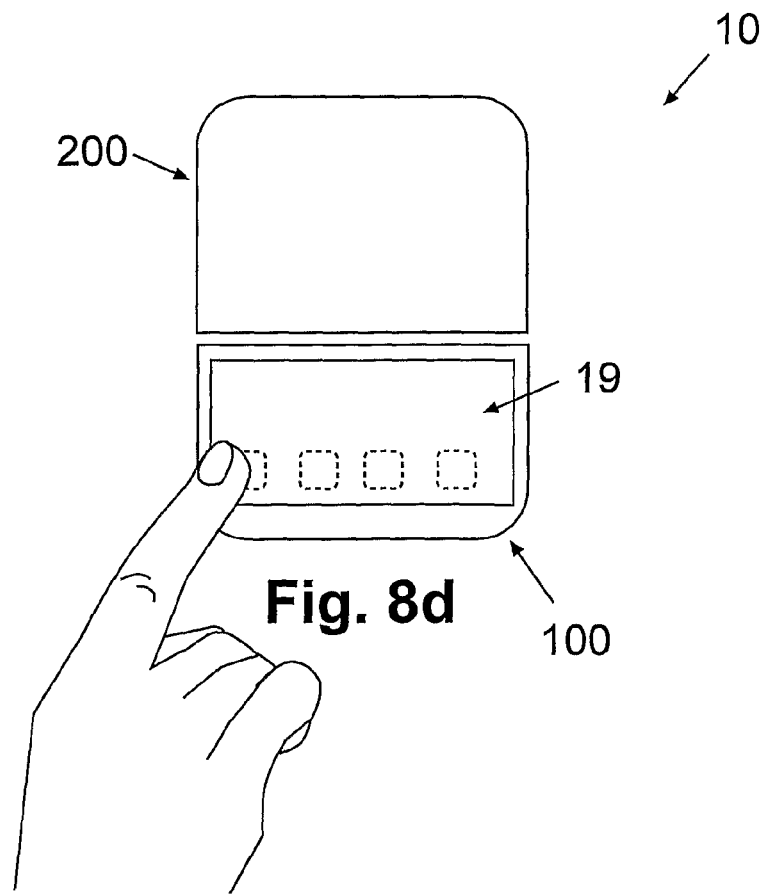

FIG. 7a shows the reusable part (100) provided with a protrusion (17) and the disposable part (200) is provided with the securing means (16). The reusable part (100) and the disposable part (200) can be paired in a "side-by-side" configuration when the protrusion (17) slides beneath and inside the circumference of the securing means (16). FIG. 7b shows the paired two part patch unit (10). FIG. 7c shows the two part patch unit (10) before parts pairing. The protrusion (17) is provided on the disposable part (200) and the securing means (16) on the reusable part (100). FIG. 7d shows the paired two part patch unit (10).

FIG. 8 shows some implementations of the device employing display (12) and various locations of operation buttons (14) on the reusable part (100). In FIG. 8a the display (12) and the buttons (14) can be located on the upper side of the reusable part (100). For example, the display (12) can be implemented by using a liquid crystal display (LCD) technology. In FIG. 8b the display (12) is on the upper side and the buttons (14) are on the lateral sides of the reusable part (100). In FIG. 8c, both display (12) and buttons (14) can be located on a flap-like auxiliary carrier portion (18) which can be hingeably connected to the main portion of the reusable part (100). FIG. 8d shows various implementations employing a touch display (19).

FIG. 9 shows the cradle unit (20) which enables the patch unit (10) to be disconnected from and reconnected to the body. The cradle unit (20) can be configured as a flat sheet that can contain an adhesive means (not shown; e.g., double-sided adhesive tape) on its bottom side. The cradle (20) can be adherable to the body before or after cannula (404) insertion. FIG. 9a shows a cross-section view of the cradle unit (20) adhered to the skin (5). The cradle unit (20) can include the base (305), the "well" (310) which can be configured as a protrusion having an opening in the cradle's base (305) for providing a passageway for the cannula (404). The cradle can be provided with an anchoring means (21 and 21') for securing the proximal end of the cannula (404) to the cradle (20) after insertion. The cradle unit (20) can also comprise connecting means for securing the patch unit (10) to the cradle unit (20). The connecting means can be configured, for example, as two latches (302 and 304). In some implementations, the cradle (20) can accommodate a portion of a position sensing mean (306) that can be connectable to a second portion (not shown) accommodated in the patch unit (10). This position sensing means can be provided for detection whether the patch unit is disconnected or connected to the cradle and accordingly for suspension and resuming the flow of fluid into the patient's body. The proximal end of the cannula (404) can include the self sealable rubber septum (402) and the "cannula hub" (401) which can be a non flexible portion that is rigidly anchored to the cradle well (310). The cannula (404) can be inserted into the body through the well (310) either manually or by using a dedicated insertion device (as disclosed in our U.S. Provisional Application 60/937,214 "Insertion device for inserting a cannula into a body", filed in Jun. 25, 2007).

Figure 9A:
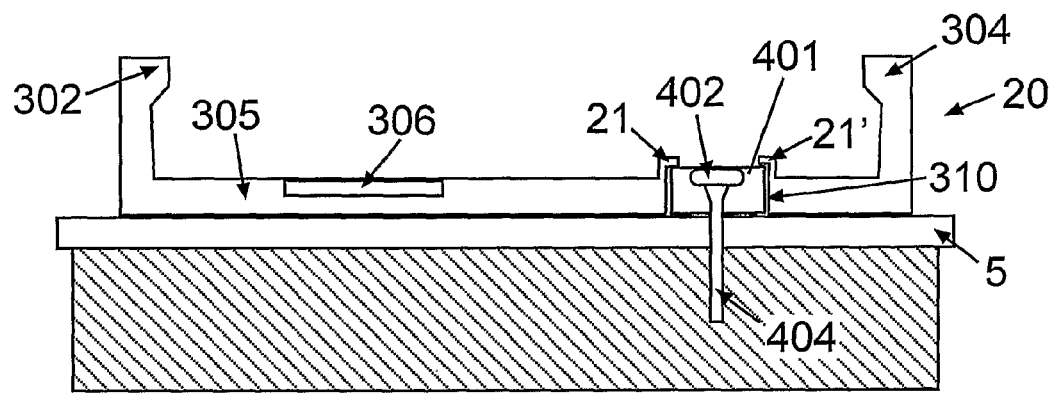
FIG. 9 shows one implementation of the cradle unit.
Figure 9B:
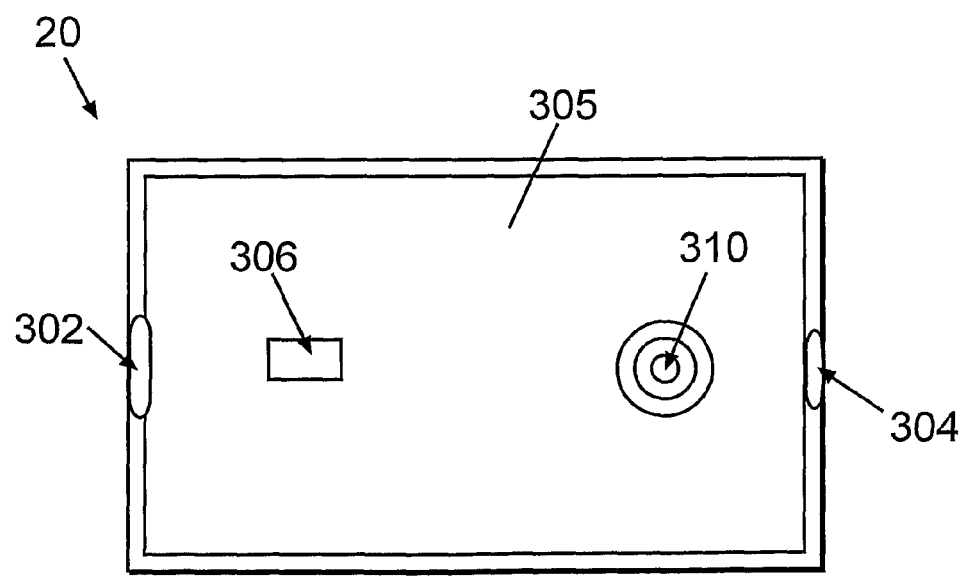
Figure 9C:
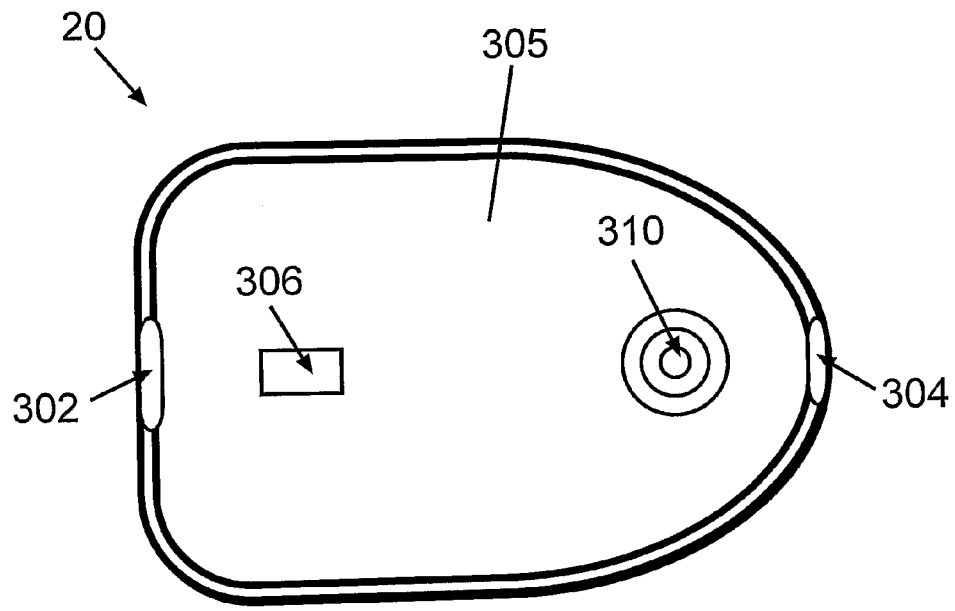
Figure 9D:
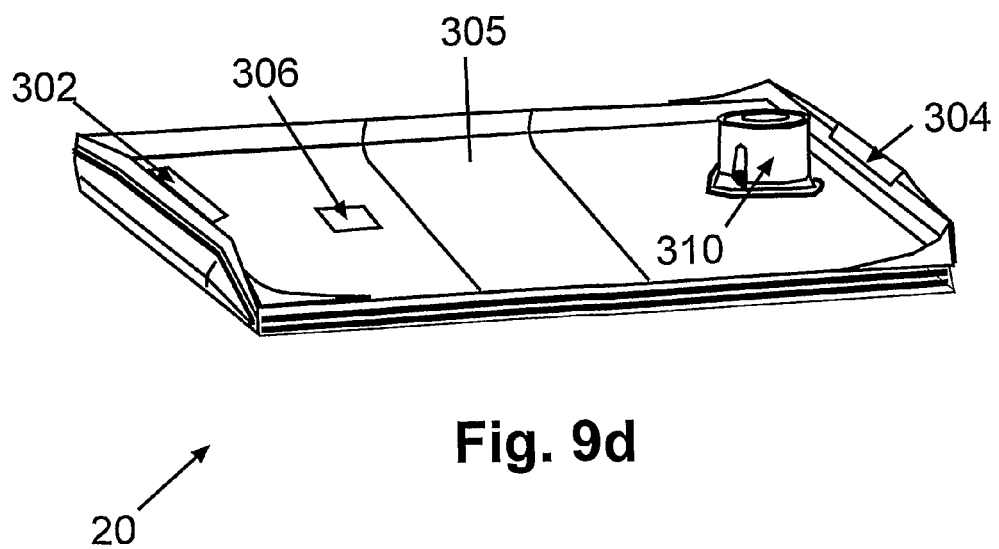
Figure 9E:
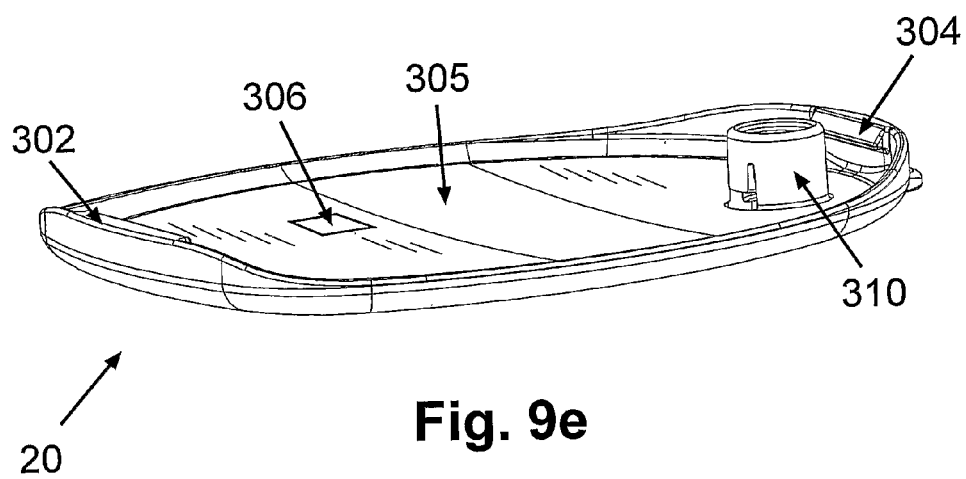

FIGS. 9b and 9c show top views of two implementations of a cradle unit (20). FIG. 9b shows a rectangular cradle unit (20) and FIG. 9c shows an elliptical cradle unit (20). FIG. 9d shows an isometric view of the rectangular cradle unit (20) and FIG. 9e shows an isometric view of the elliptically shaped cradle unit (20). The cradle (20) can be provided with a well (310), with connecting means (302, 304), and with a position sensor (306). The rectangular shaped cradle unit (20) can be more likely to be used with a dispensing unit (10) that can employ a plunger/piston driving mechanism for syringe type pumping mechanism since in this configuration the housing (213) of the disposable part (FIG. 1, No. 213) can serve as reservoir for storing fluid to be dispensed.

FIG. 10 shows one implementation of the cannula (404) insertion and the cradle (20) adherence. The cannula (404) insertion can be carried out manually (not shown), or automatically with the aim of the insertion device (800). FIG. 10a shows an example of the insertion device ("inserter") (800) before it is being loaded with the "cannula cartridge unit" (700). The cannula cartridge unit (700) can include a soft cannula (404), penetrating member (702) with a grip portion (704), rubber septum (402), cannula hub (401) for anchoring. The cannula cartridge unit can comprise a "protector" (701) that maintains sterility, avoids unintentional pricking, and facilitates inserter (800) loading. The "cannula cartridge unit" (700) is described in our U.S. Provisional Application 60/937, 155 "Protector for cannula and penetrating member insertable in the body of a patient", filed in Jun. 25, 2007. The insertion method is described in our U.S. Provisional Application 60/937,214 "Insertion device for inserting a cannula into a body", filed in Jun. 25, 2007.

The insertion device (800) can include the housing (804) to which the cradle (20) is loaded, the slot (806) to which the cannula cartridge unit (700) is loaded, and the button (802) which initiates the insertion.

Figure 10A:
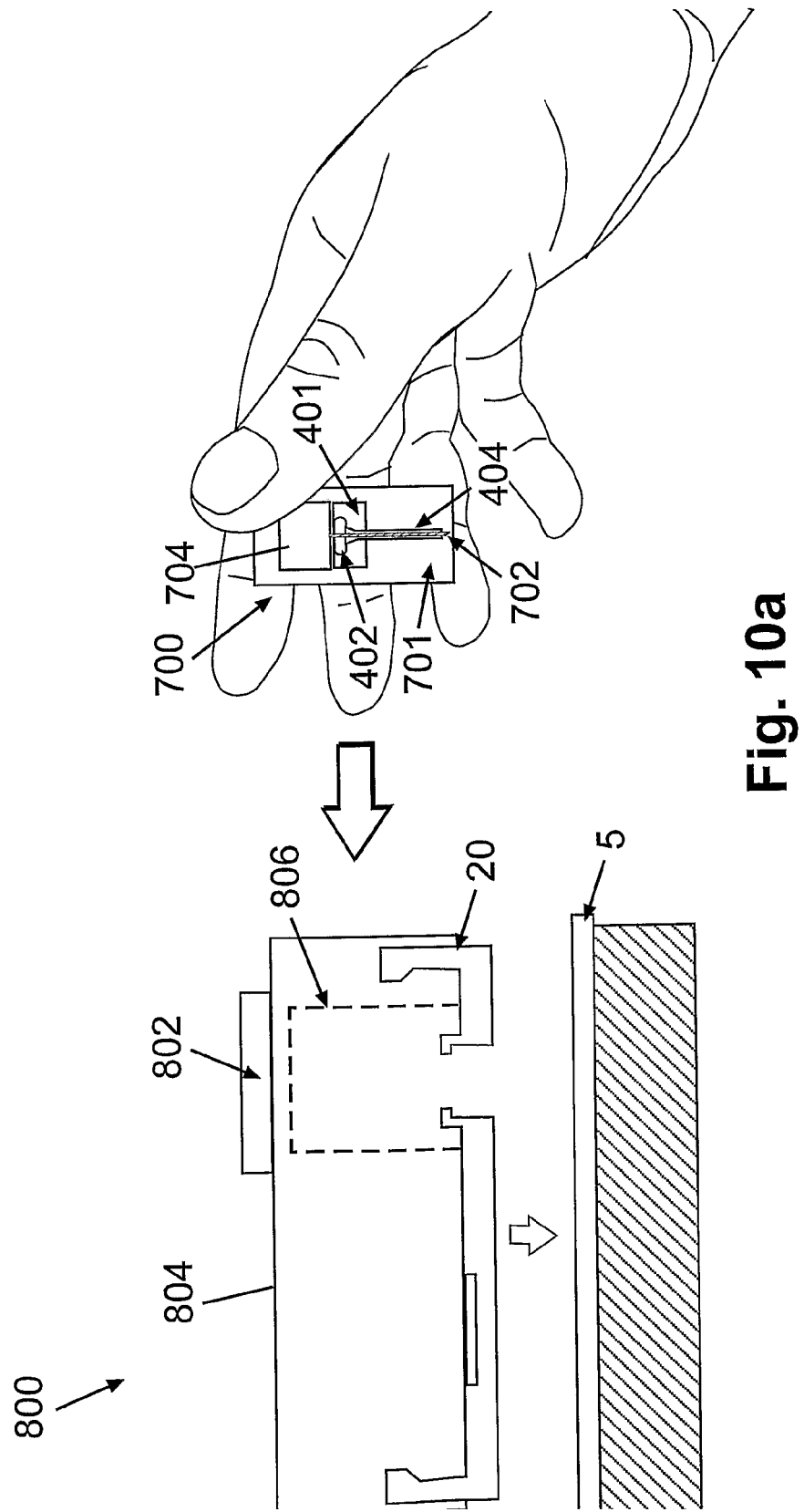
FIG. 10 shows one implementation of the cannula insertion process using an insertion device.
Figure 10B:
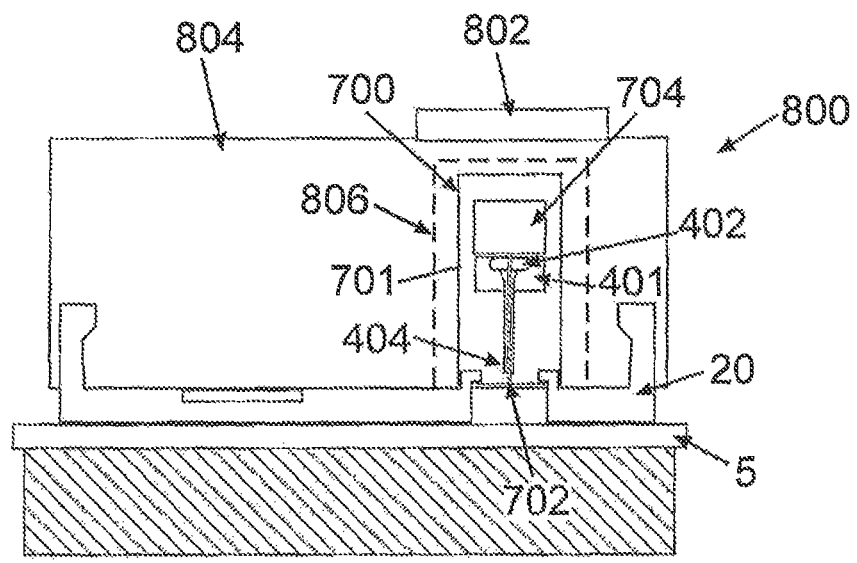
Figure 10C:
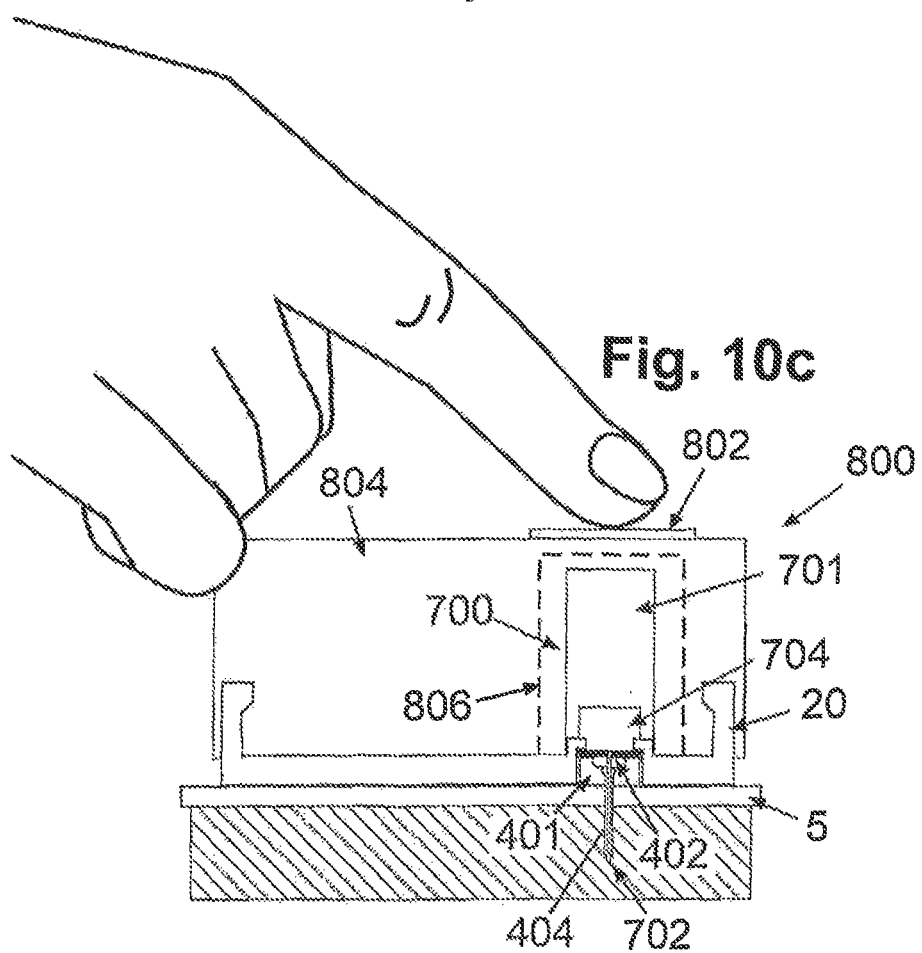
Figure 10D:
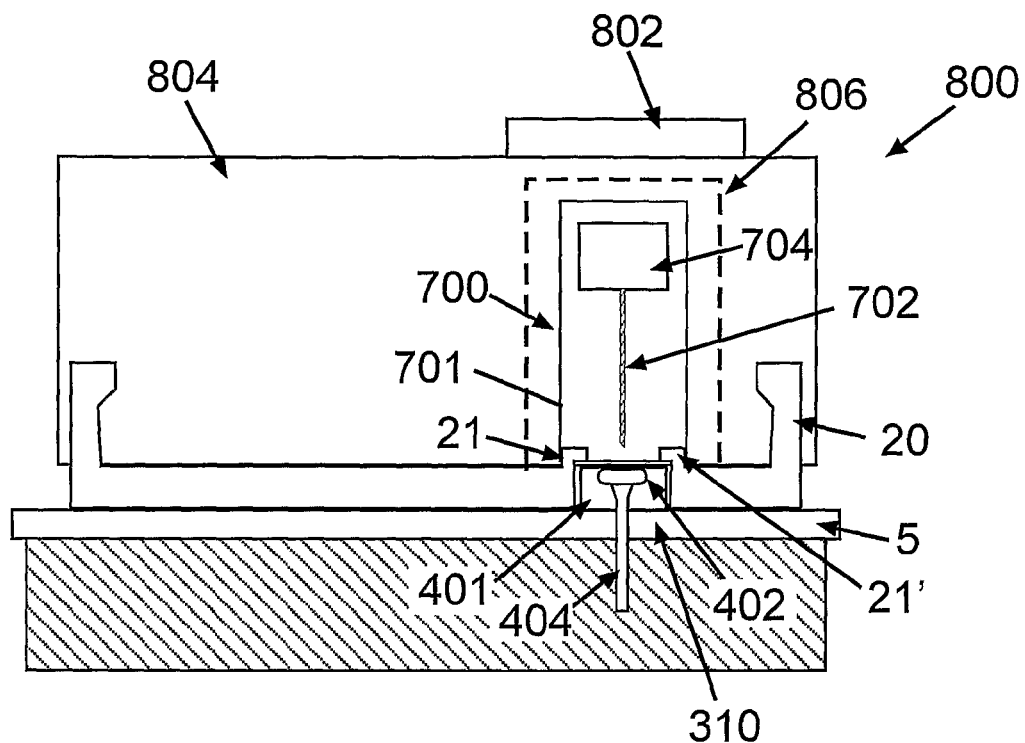

FIG. 10b shows the insertion device (800) loaded with the cannula cartridge unit (700) and with the cradle unit (20) before cannula insertion. The cradle unit (20) can be adhered to the skin (5). FIG. 10c shows the insertion of the cannula (404) into the patient's skin (5) by pressing the button (802). FIG. 10d shows the retraction of the penetrating member (702) and grip portion (704). The soft cannula (404) is positioned within the subcutaneous compartment. The cannula hub (401) is rigidly connected to the anchoring means (21 and 21') of the well (310).

Figure 11A:
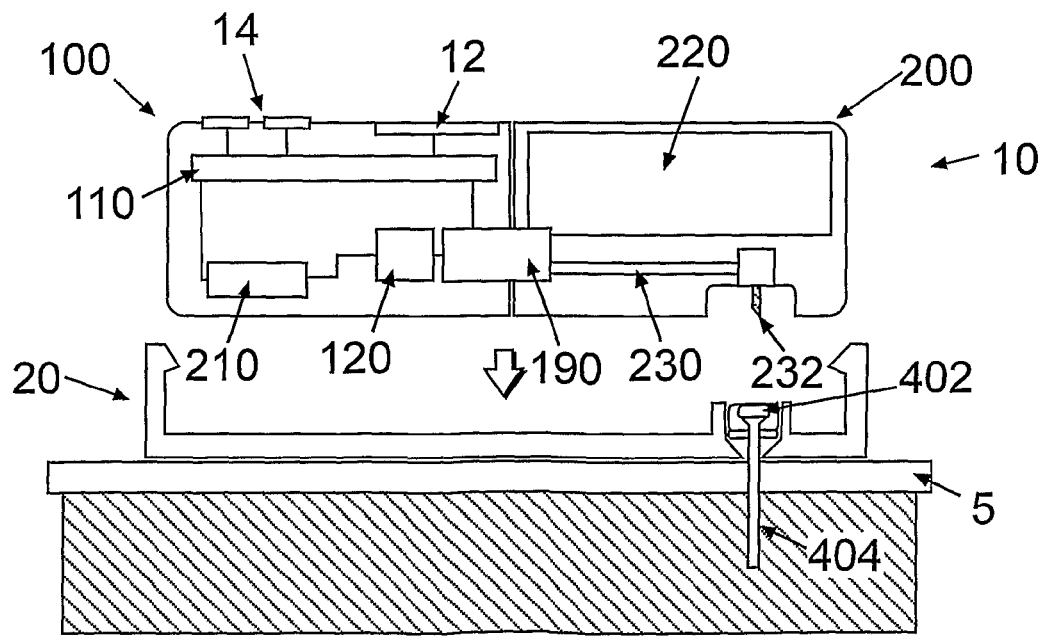
FIG. 11a shows one implementation of connection of patch unit to cradle unit.
Figure 11B:
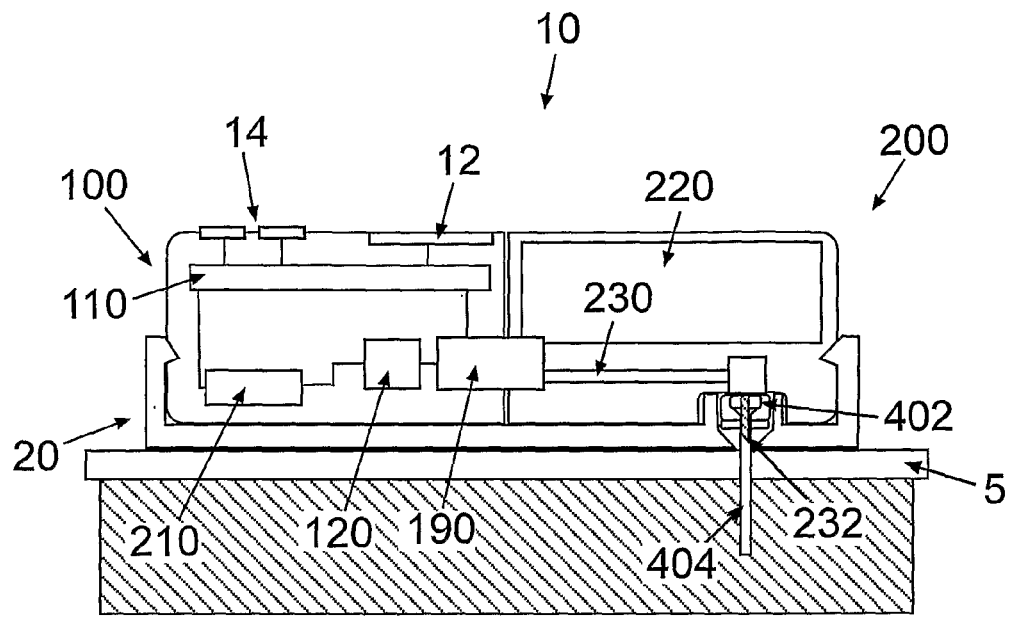
FIG. 11b shows one implementation of the connected patch unit and cradle with the operating buttons and the display facing up.
Figure 11C:
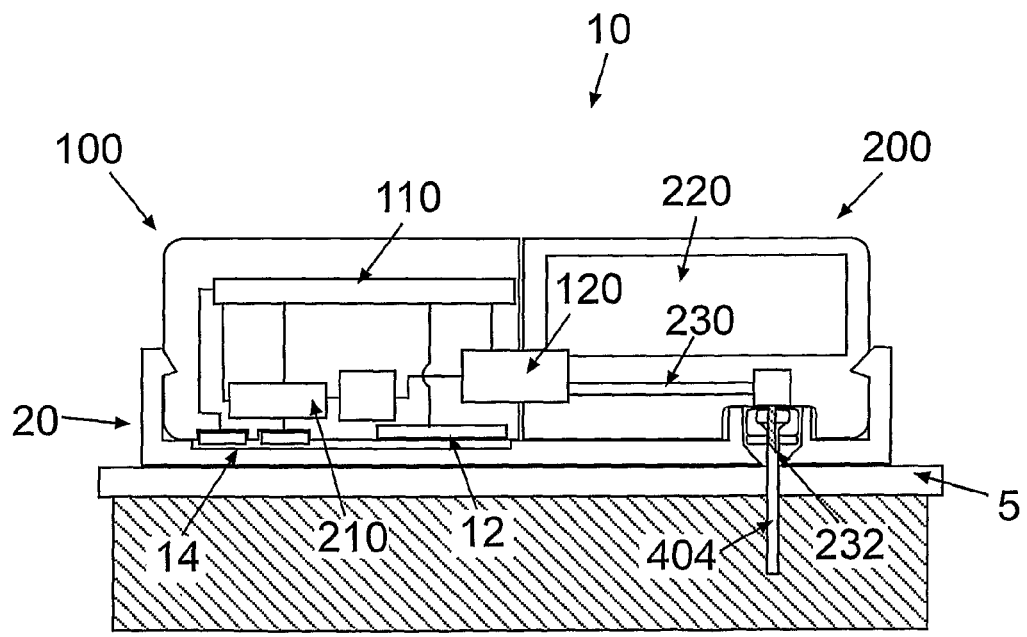
FIG. 11c shows one implementation of the connected patch unit and cradle unit with operating buttons and the display facing down.

FIG. 11 shows the two part patch unit (10) and cradle unit (20) before (FIG. 11a) and after (FIG. 11b and FIG. 11c) connection. The reusable part (100) can include the power source (210), driving mechanism (120), pumping mechanism (190), Printed Circuit Board (PCB)/processor (110), operating buttons (14), and display (12). The disposable part (200) can include the reservoir (220), delivery tube (230), and connecting lumen (232). The cradle unit (20) can be connected to the soft cannula (404) which has a rubber septum (402) at its proximal end.

FIG. 11a shows the two part patch unit (10) before connection to the cradle unit (20) including the reusable part (100), the disposable part (200), and cradle unit (20).

The disposable part (200) can contains the reservoir (220), the tube (230), and the connecting lumen (232) that can pierce the septum (402) of the cannula (404). The reusable part (100) contains PCB (110), driving mechanism (120), pumping mechanism (190), and power source (210). The upper side of the reusable part (100) is provided with a display (12) and buttons (14).

FIG. 11b shows the two part patch unit (10) connected to the cradle unit (20). The connecting lumen (232) pierces the septum (402) providing fluid communication between the reservoir (220), the cannula (404) and the body.

FIG. 11c shows another implementation of patch (10) and cradle (20) connection. The display (12) and operating buttons (14) on the reusable part (100) are facing the cradle (20) avoiding unintentional button pressing and patch (10) operation.

Figure 12A:
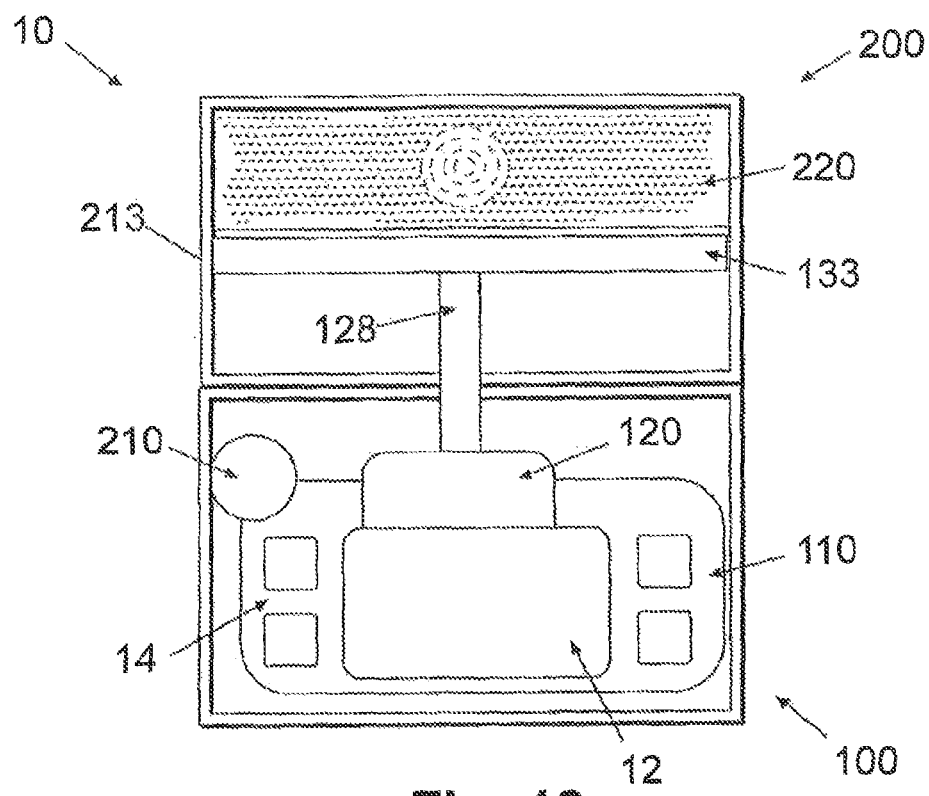
FIG. 12a shows one implementation of the two part patch unit with piston mechanism and the components within each part.

FIG. 12a shows another implementation of the two part patch unit (10) provided with a piston/plunger pumping mechanism. The interior of the disposable part's housing (213) can function as a reservoir (220). The disposable part (200) can contain the piston plunger (133) and the piston rod (128). The reusable part (100) can include the processor (110), the battery (210), the display (12), the operation buttons (14), and the driving mechanism (120). In some implementations, the battery (210) can be provided in the disposable part (200) and connected to the processor (110) via connectors (not shown).

Figure 12B:
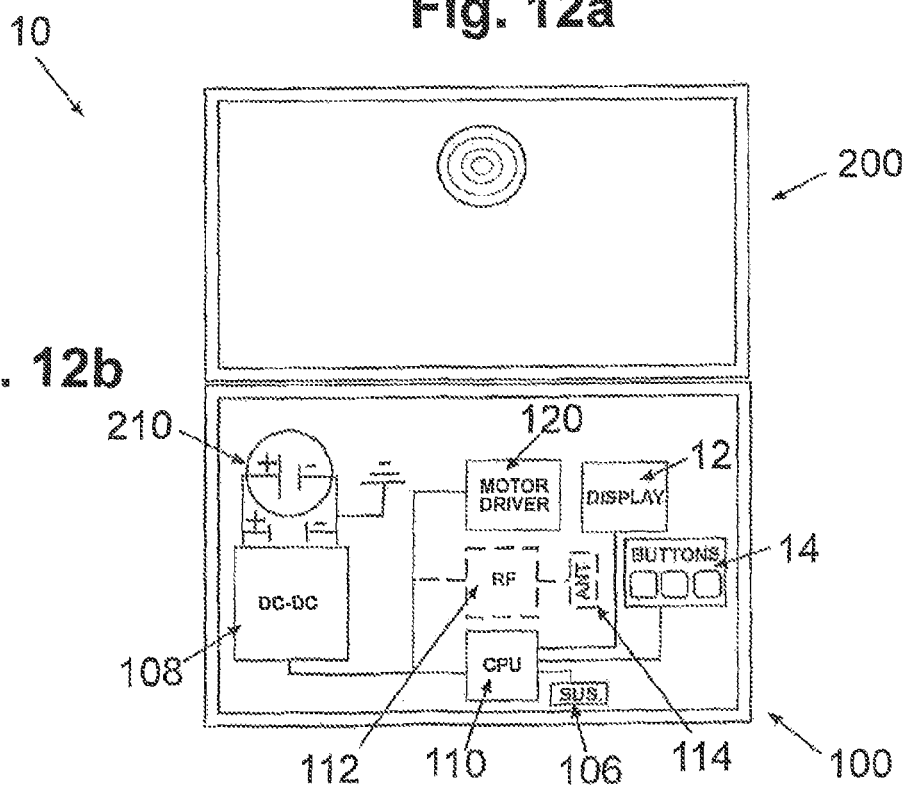
FIG. 12b shows one implementation of the two part patch unit and the electronic components within each part.

FIG. 12b shows the electronic components of the two parts patch unit (10). The disposable part (200) need not include electrical means. The reusable part (100) can include the battery (210), the power component (108) that transfers current to the processor (110). The processor (110) can be connected to the motor driver (120), the display (12), the operating buttons (14), and the position sensor (106). In another implementation, the RF component (112) and the antenna (114) can be provided for communication with a remote control (not shown). In another implementation the battery (210) can be provided in the disposable part (200).

FIG. 13 shows consecutive steps of device operation sequence which begins with reservoir filling, then proceeds to parts pairing, mounting and programming.

Figure 13A:
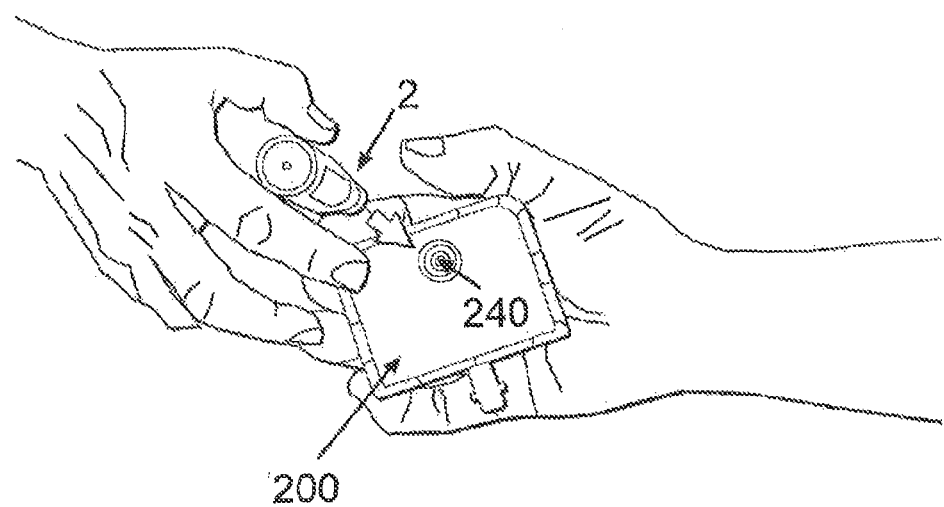
FIG. 13 shows one implementation of the process and device operating with the piston mechanism.
Figure 13B:
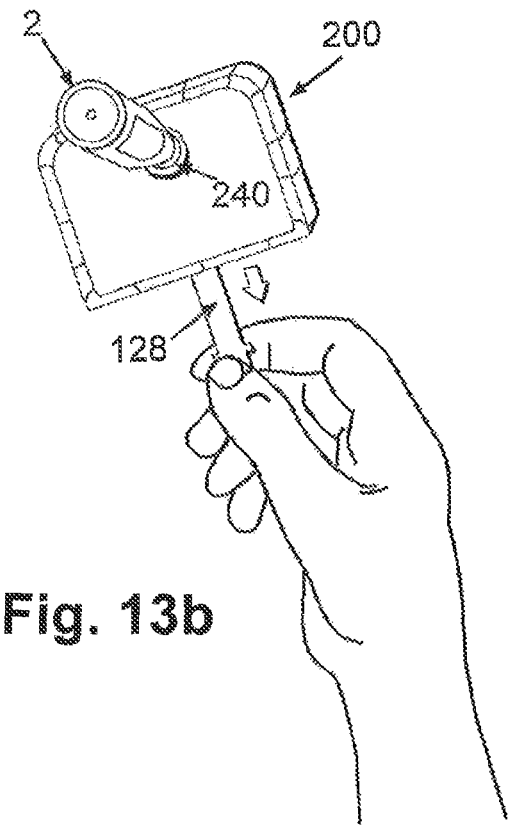
Figure 13C:
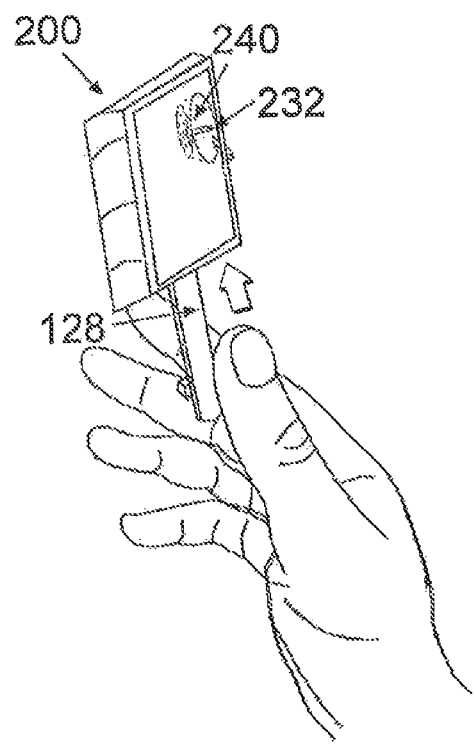

FIGS. 13a and 13b show one implementation of fluid drawing from a vial (2). FIG. 13a shows the attachment of a vial (2) to the disposable part (200). The disposable part (200) is provided with a port (240) for direct attachment of the vial (2). Attachment of vial (2) and well (not shown) can be done by the same port (240). Fluid withdrawal can be done also with a dedicated adapter (not shown) as disclosed in our International Application number PCT/IL07/001027 "Methods and devices for delivering fluid to a reservoir of a fluid delivery device" filed in Aug. 16, 2007. FIG. 13b shows the disposable part (200) in an upright position and fluid withdrawal from the vial (2) into the reservoir (220) by pulling the piston rod (128). FIG. 13c shows a manual priming process. After complete filling of reservoir (220), the user presses the piston rod (128) until drops are dripping from the connecting lumen (232) ensuring that no air bubbles remain within the fluid path.

Figure 13D:
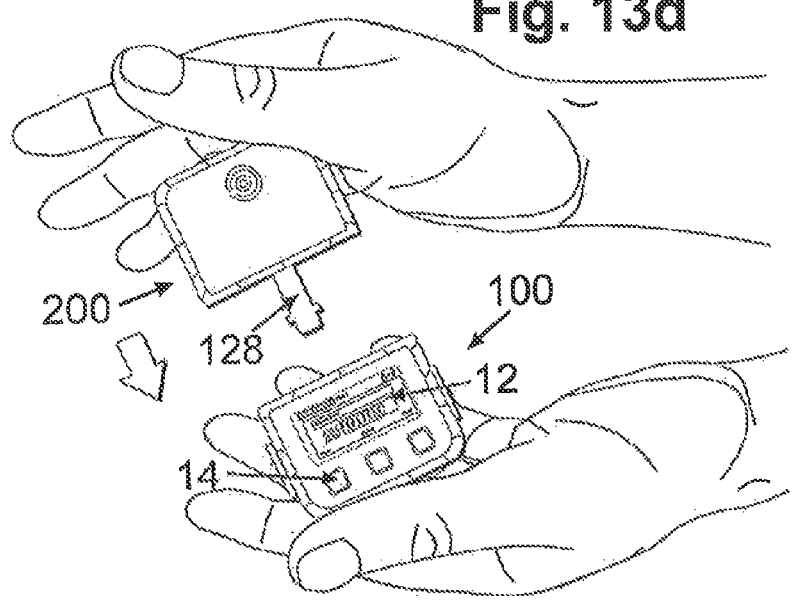
Figure 13E:
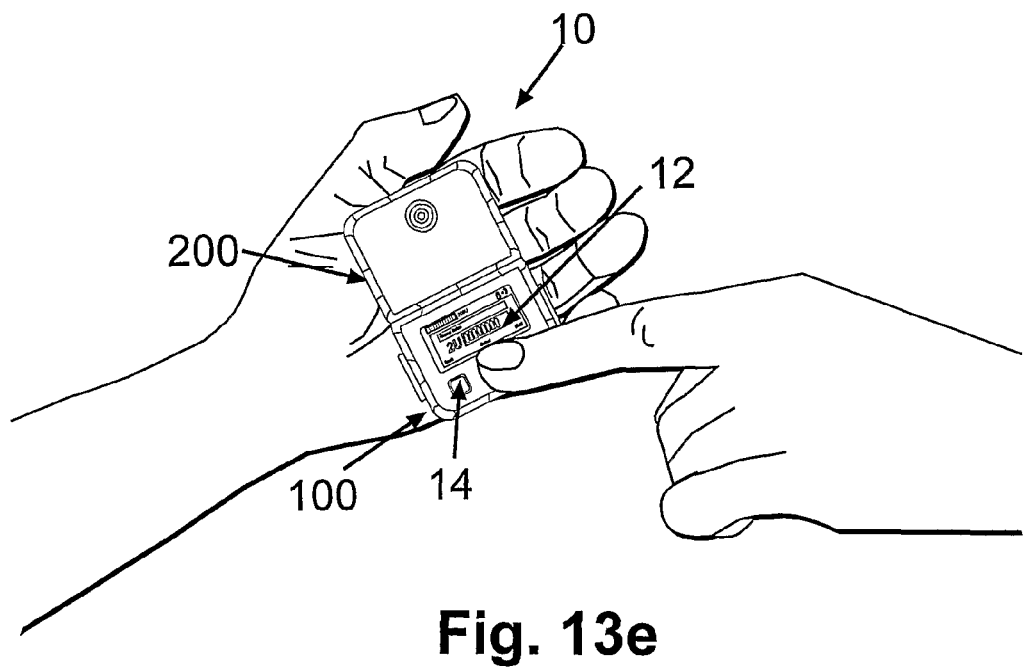
Figure 13F:
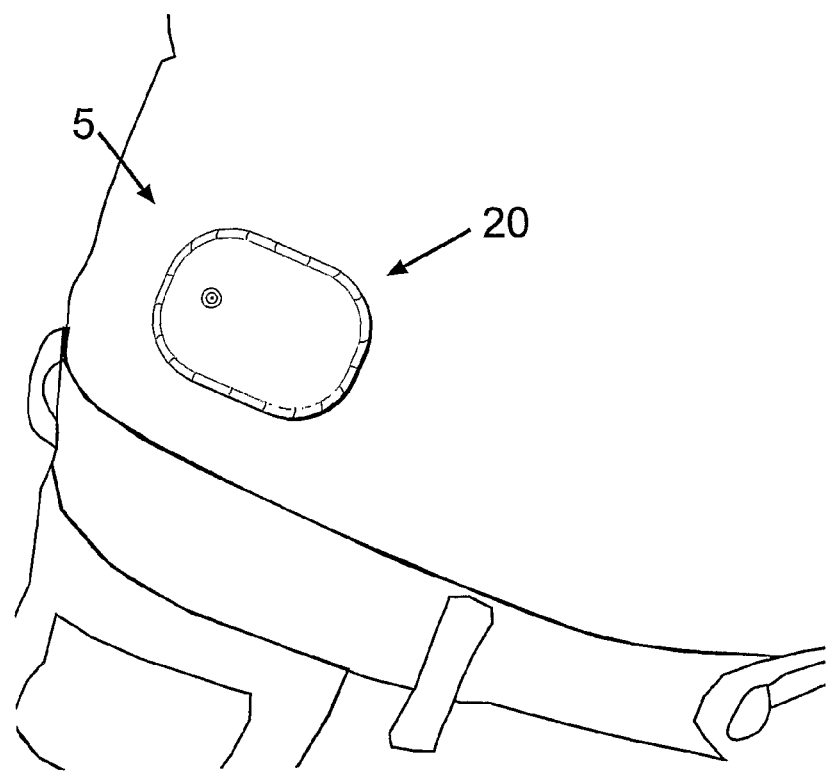
Figure 13G:
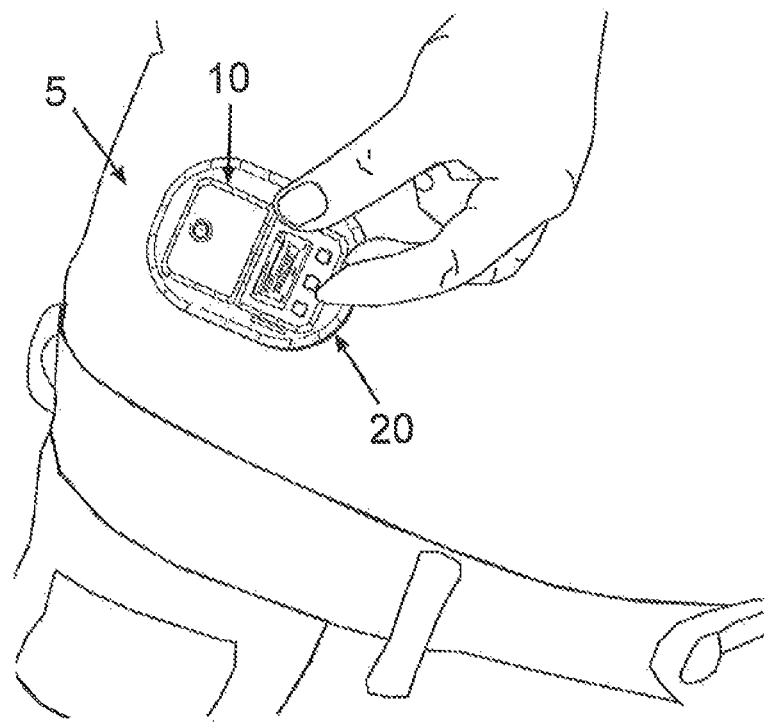
Figure 13H:
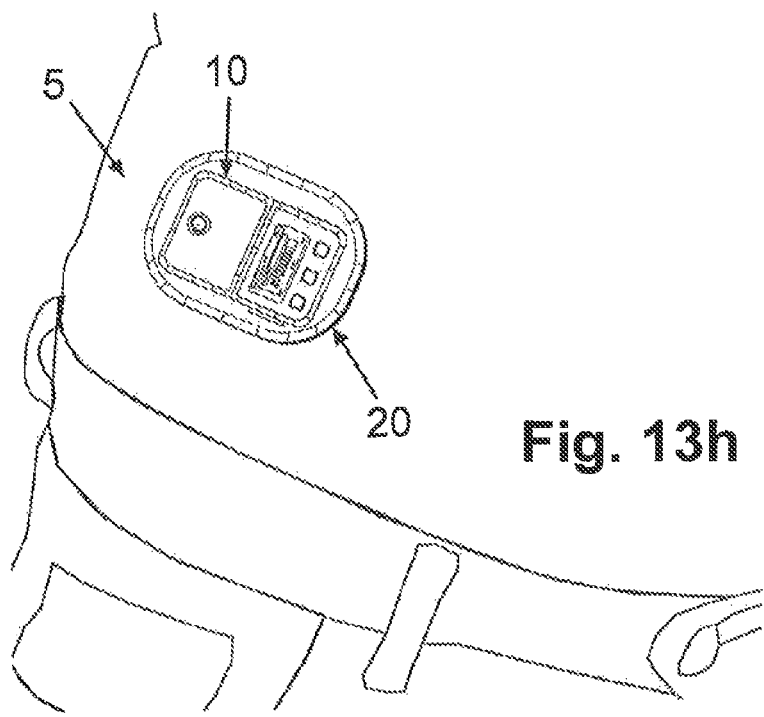
Figure 13I:
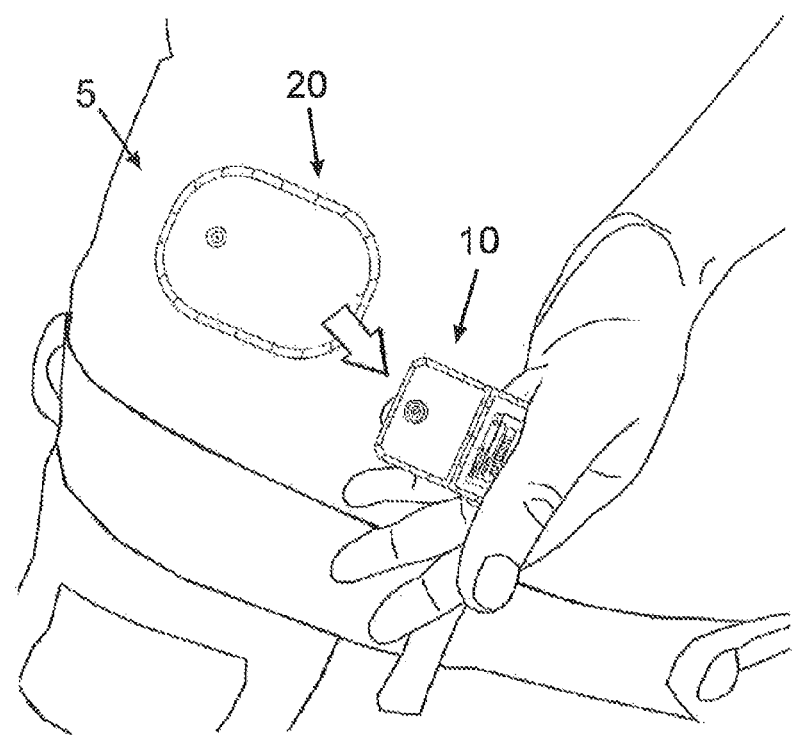

FIG. 13d shows pairing of the disposable part (200) and the reusable part (100). FIG. 13e shows the patch (10) setup (i.e. flow programming, which can be carried out by operation buttons). FIG. 13f shows the cradle unit (20) adhered to the skin (5). FIG. 13g shows the patch (10) connection to the cradle unit (20). FIG. 13h shows the patch (10) connected to the cradle (20) on the user skin (5). FIG. 13i shows disconnection of the patch (10) from the cradle (20). In one implementation, the patch (10) can be provided with a position sensor (not shown) which causes flow suspension upon patch (10) disconnection.

Figure 13J:
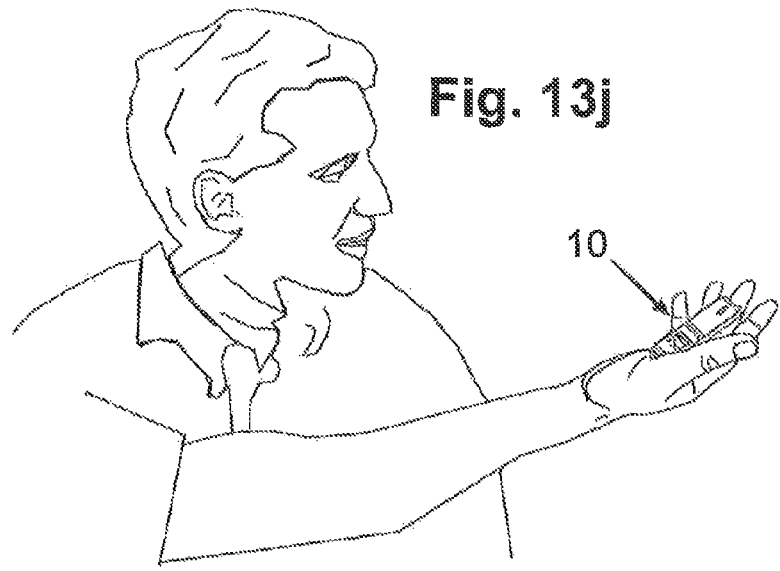

FIG. 13j shows a user checking the patch (10) status by observation of the display provided at the patch unit. FIG. 13k shows the user programming the patch (10), for example inputting flow instructions by operation buttons. FIG. 13l shows reconnection of the patch (10) to the cradle (20). After connection, flow delivery can be resumed automatically as disclosed in our Co-Pending U.S. Provisional Application No. 60/963,045 filed on August 1st, and titled "Detachable Portable Infusion Device", incorporated herein by reference in its entirety.

FIG. 14a shows an isometric view of a disposable (200) and reusable (100) parts before connection. The reusable part (100) includes operating buttons (14) and display (12).

FIG. 14b shows the dispensing unit (10) after parts pairing. The reusable part (100) can contain either a piston-plunger pumping mechanism or a peristaltic pumping mechanism.

FIGS. 15-18 show different implementations of a two part patch unit (10) provided with a piston-plunger pumping mechanism.

Figure 15A:
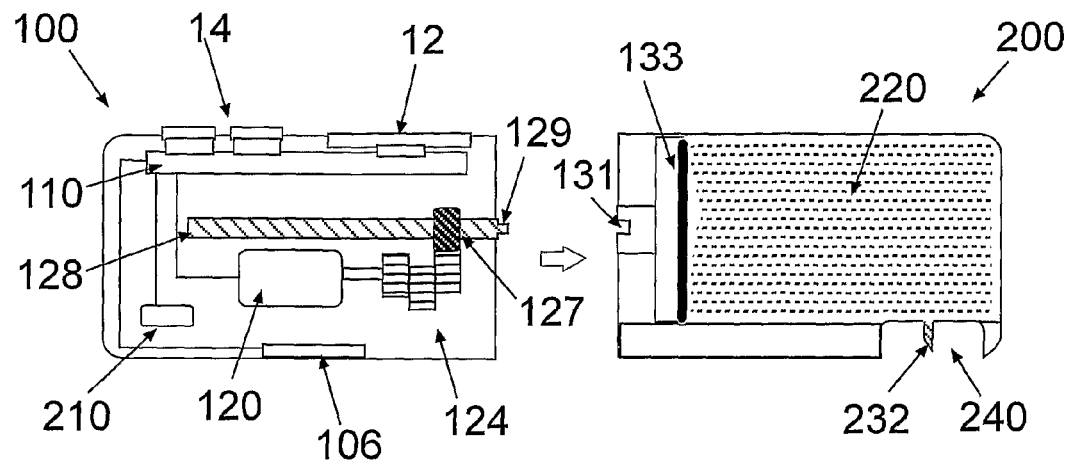
FIG. 15 shows one implementation of paring and connection of the two part patch unit employing a piston and plunger mechanism.

FIG. 15a shows the reusable (100) and disposable (200) parts before connection. The reusable part (100) contains display (12), operating buttons (14), position sensor (106), processor (110), driving mechanism (120), battery (210), gear (124), screw nut (127), plunger rod (128) and plunger jut (129). The disposable part (200) can include the reservoir (220), the piston (133), the plunger fosses (131), and the connecting lumen (232) positioned in the outlet port (240).

Figure 15B:
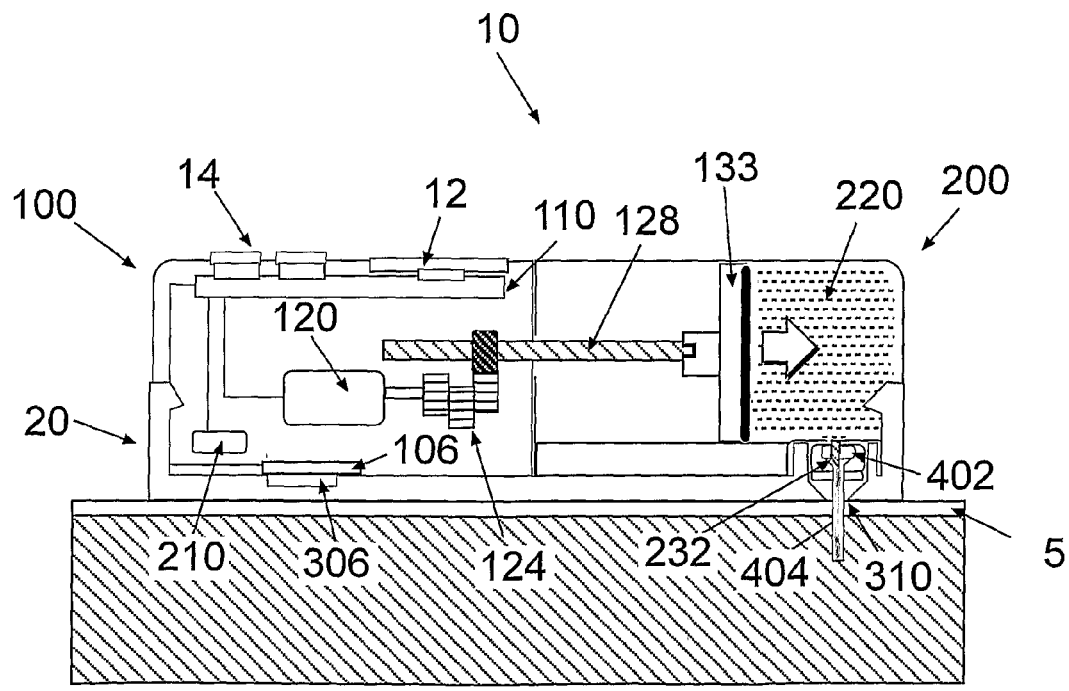

FIG. 15b shows the paired two part patch (10) connected to the cradle (20). The connecting lumen (232) pierces the cannula septum (402). The two parts of the position sensor (106 and 306) are in close proximity notifying the processor (110) on a "connected position" and thus allowing fluid delivery. The plunger rod (128) pushes the piston (133) and fluid is dispensed from the connecting lumen (232) via the cannula (404) and into the body.

FIG. 16-18 show another implementation of pairing a two part patch (10) employing a plunger-piston pumping mechanism. The reusable part (100) is placed on top of the disposable part (200). The display (12) and buttons (14) occupy the entire upper face surface area of the reusable part (100).

Figure 16A:
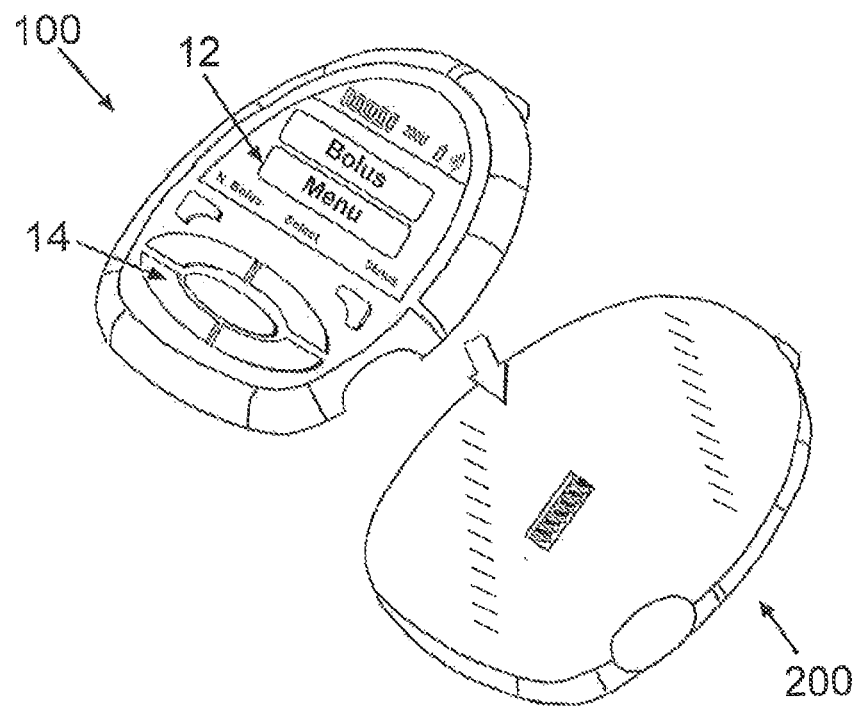
FIG. 16 shows an isometric view of another implementation of a two part patch unit before and after connection.
Figure 16B:
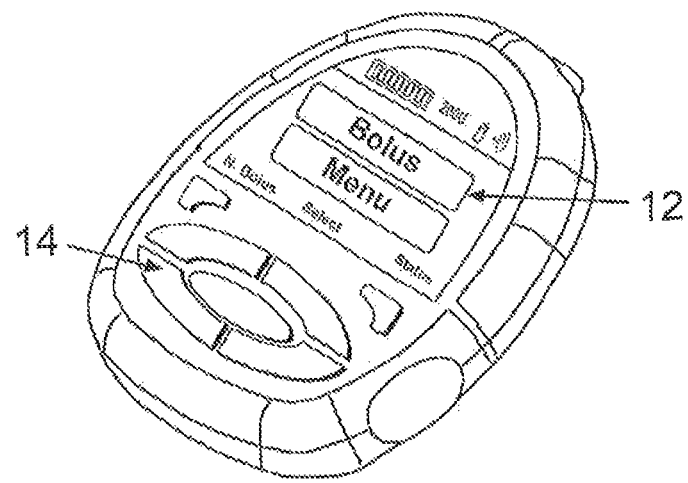

FIG. 16a shows the disposable (200) and reusable (100) parts before pairing. FIG. 16b shows the paired two part patch (10).

Figure 17A:
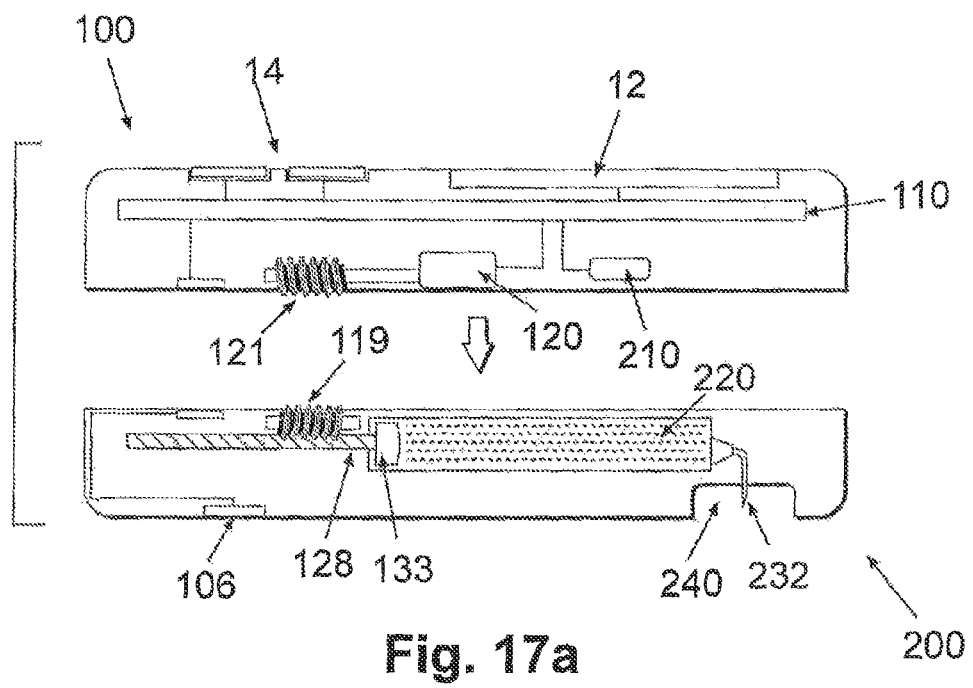
FIG. 17 shows one implementation of the two part patch unit before and after connection.

FIG. 17a shows the reusable (100) and disposable (200) parts before pairing. The reusable part (100) contains display (12), operating buttons (14), processor (110), battery (210), driving mechanism (120), and worm (121). The disposable part (200) includes worm (119), reservoir (220), plunger rod (128), piston (133), position sensor (106), and connecting lumen (232) provided in the outlet port (240).

Figure 17B:
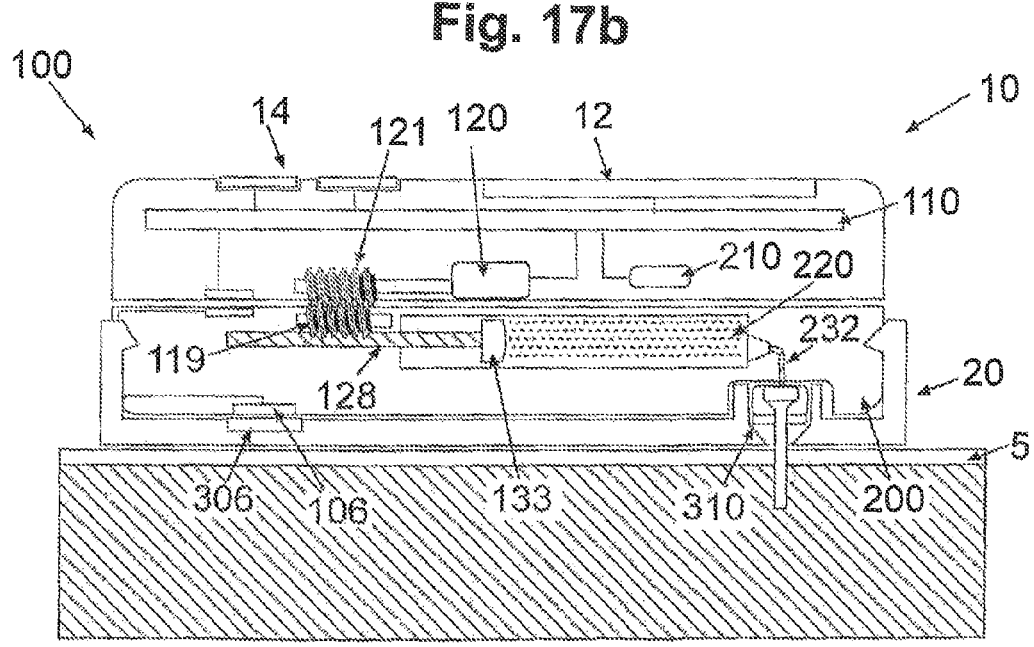

FIG. 17b shows the two part patch (10) connected to the cradle (20). The reusable part protruding worm (121) rotates the disposable part worm (119) and consequently the plunger (133) advances and positively displaces fluid from reservoir (220) to the connecting lumen (232).

Figure 18A:
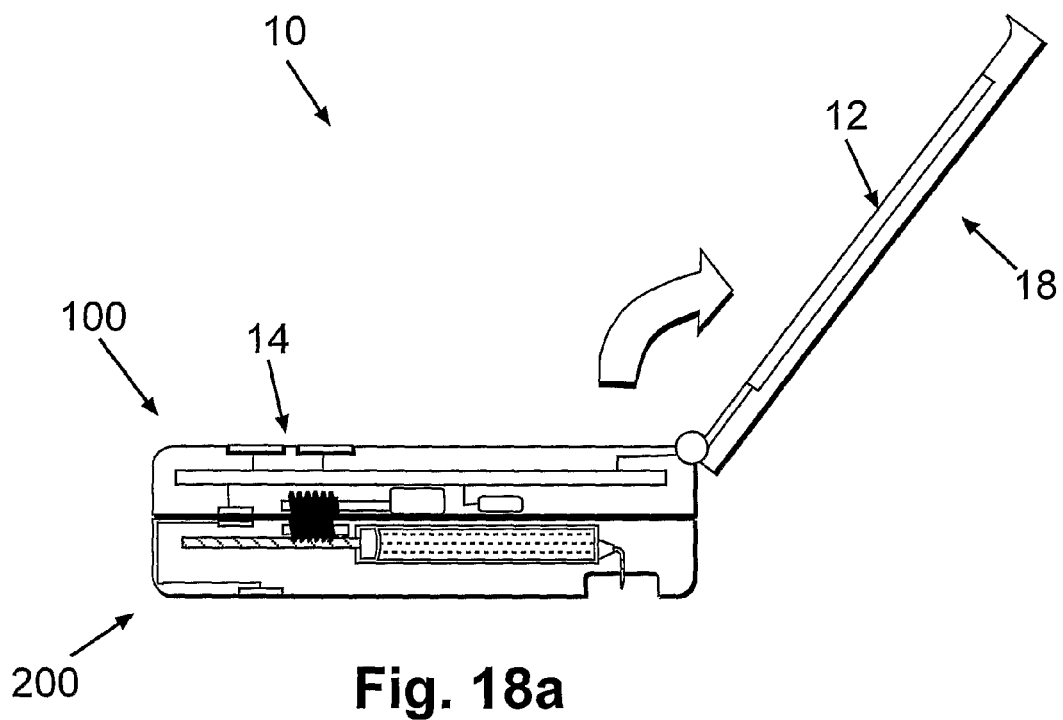
FIG. 18 shows one implementation of the two part patch unit with the display implemented in the reusable part and covered with the flip.
Figure 18B:
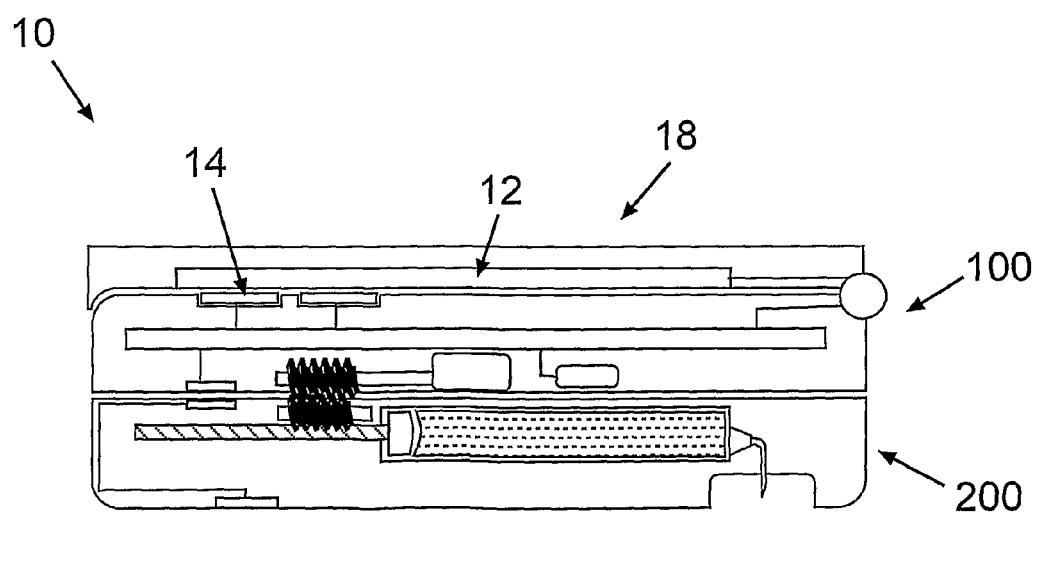

FIG. 18a shows another implementation of a two-part patch (10). The display (12) of the reusable part (100) is provided with a flip (18) allowing a larger view display (12). The operating buttons (14) are located on the upper surface of the reusable part (100). FIG. 18b shows the flip (18) in a close position protecting the operating buttons (14) and display (12) from unintentional operation. The displacement of the display (12) and operating buttons (14) may be interchangeable both on the flip (18) and on the reusable part (100).

Figure 19A:
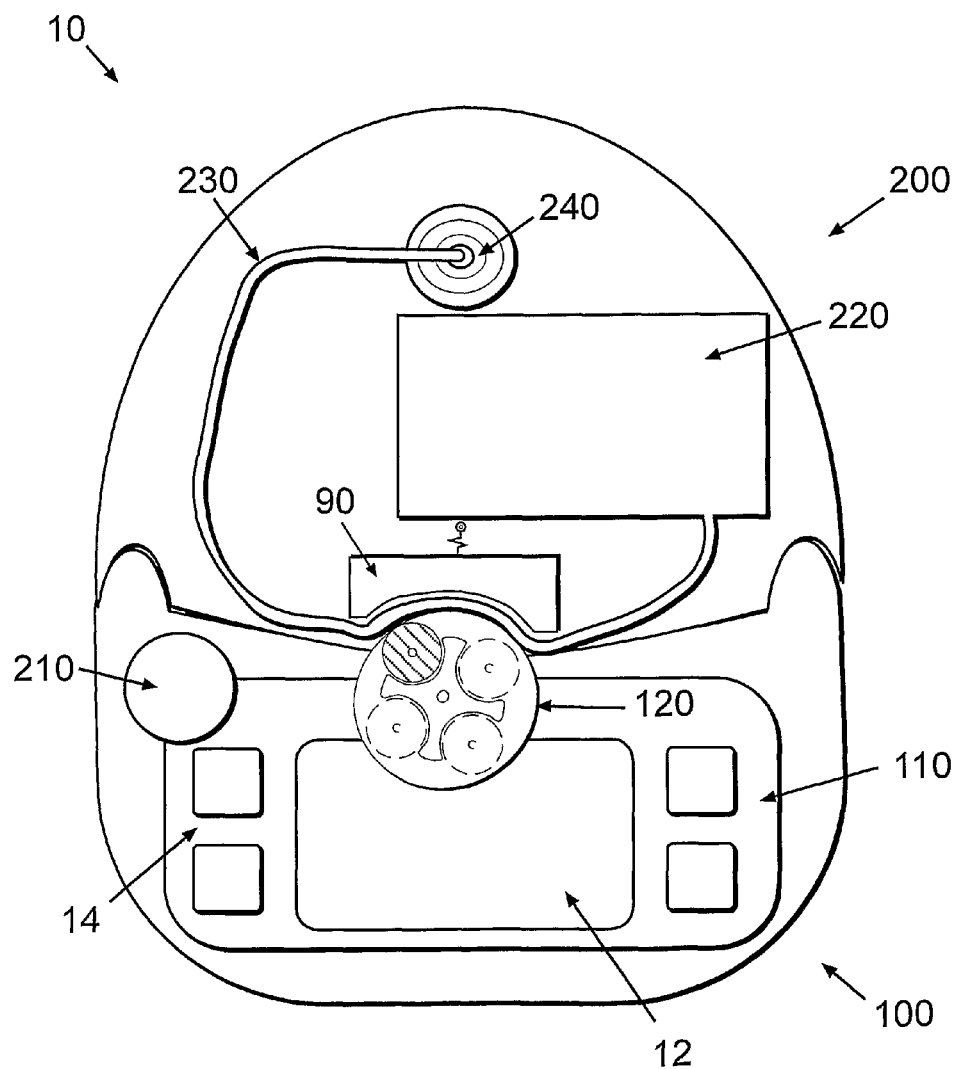
FIG. 19a shows one implementation of the two part patch unit and the components within each part. The patch unit includes a peristaltic mechanism.

FIG. 19-21 show different implementations of a two-part patch unit (10) provided with a peristaltic pumping mechanism. FIG. 19a shows the two part patch unit (10). The disposable part (200) includes reservoir (220), delivery tube (230) and outlet port (240). The reusable part (100) includes processor (110), power source (210), display (12), operating buttons (14), and pumping mechanism which is a rotary wheel (120) that positively displaces fluid from the reservoir (220) to the outlet port (240) by consecutive squeezing of delivery tube (230). In other implementations the power source (210) is provided within the disposable part (200).

Figure 19B:
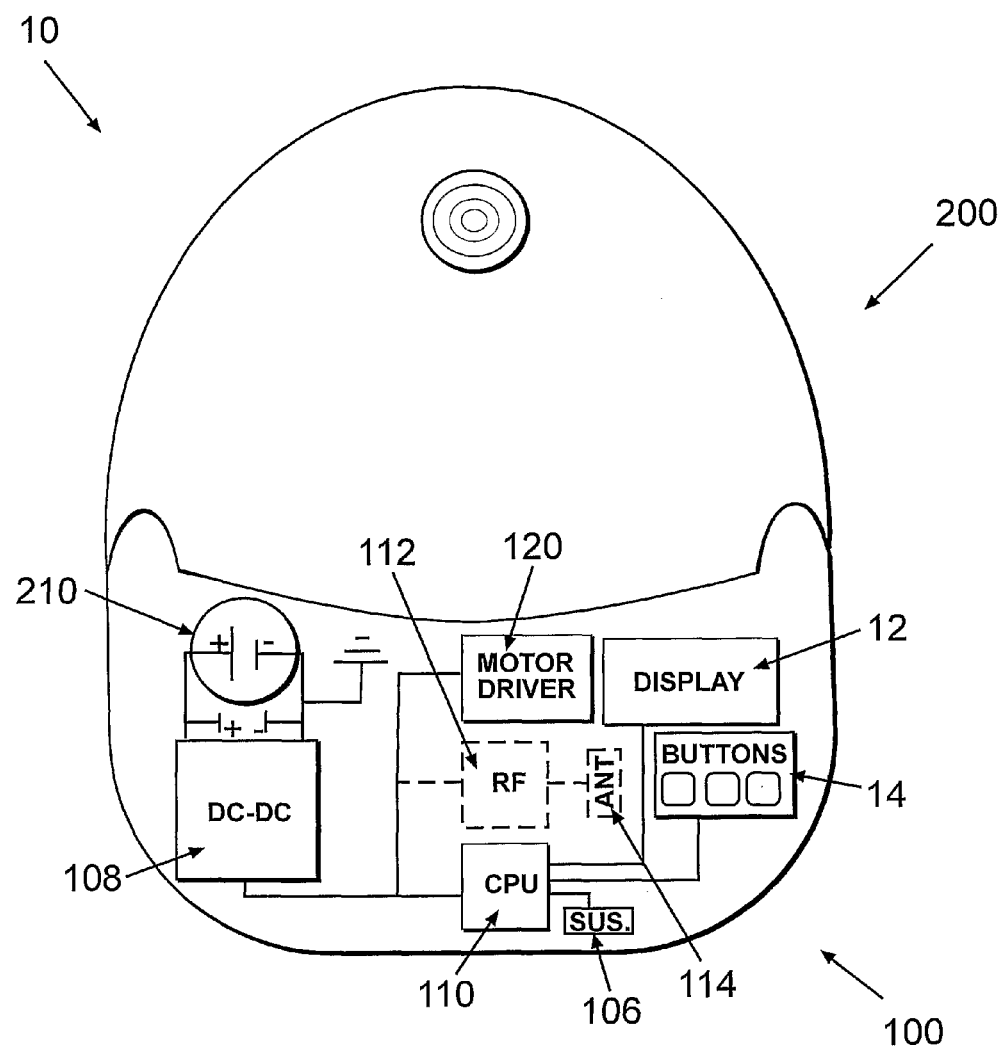
FIG. 19b shows one implementation of the two part patch unit and the electronic components within each part.

FIG. 19b shows the electronic components of the two parts patch unit (10). The disposable part (200) does not need to include electronics. The reusable part (100) can include the battery (210), the power component (108) that the transfers current to the processor (110). The processor (110) can be connected to the motor driver (120), display (12), operating buttons (14), and position sensor (106). In another implementation RF component (112) and antenna (114) are provided for communication with a remote control (40).

In other embodiments, the battery (210) can be recharged with a dedicated charger or can be provided with a USB or other known in the art connection means for connection to a PC or other electronic means for charging the battery (210).

FIG. 20 shows consecutive steps of device operation beginning with reservoir filling, parts pairing, mounting and programming.

Figure 20A:
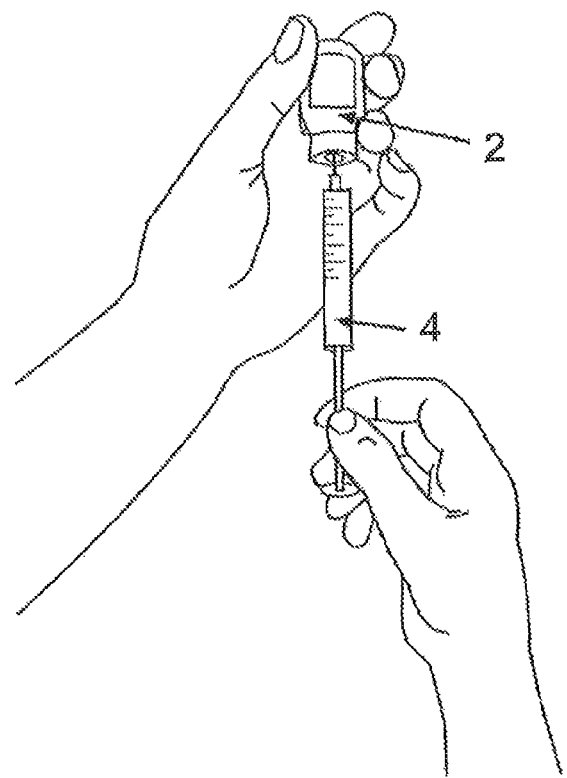
FIG. 20 shows one implementation of the device with the peristaltic mechanism implemented in the patch unit.
Figure 20B:
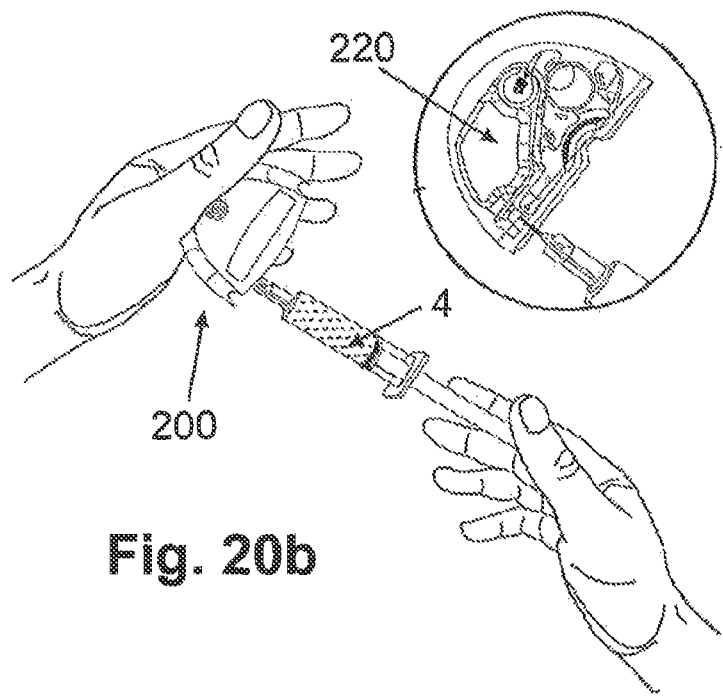
Figure 20C:
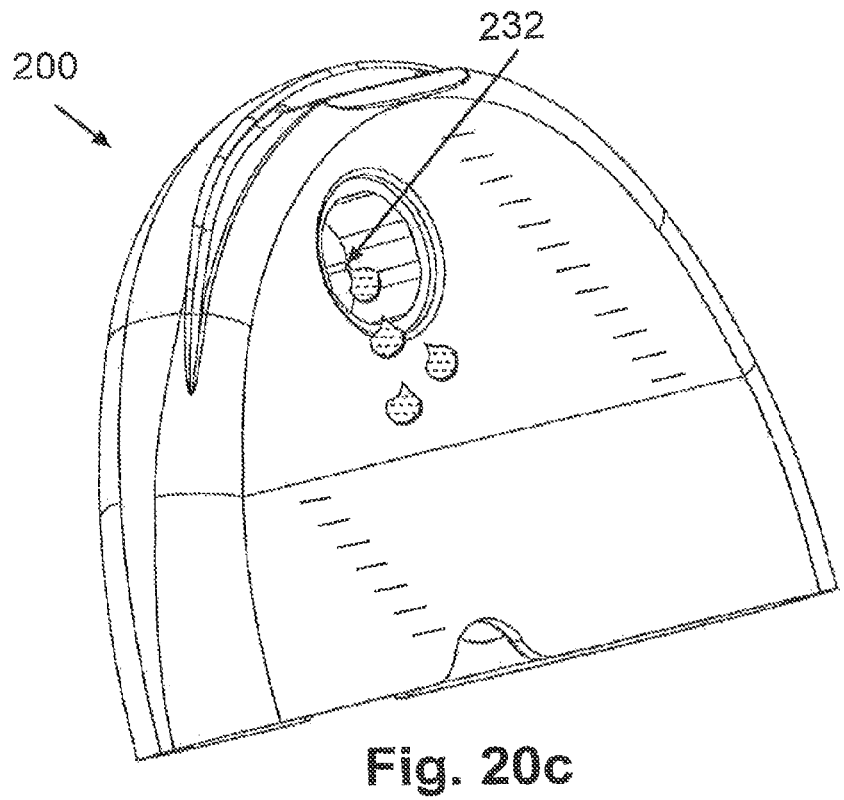

FIG. 20a shows fluid drawing from a vial (2) to a syringe (4). FIG. 20b shows filling of the reservoir (220) with a syringe (4). Fluid withdrawal can be done also with a dedicated adapter as disclosed in international patent application number PCT/IL07/001027 "Methods and devices for delivering fluid to a reservoir of a fluid delivery device" filed in Aug. 16, 2007. FIG. 20c shows a manual priming process—after complete filling of reservoir (220) and delivery tube (230), drops are dripping from the connecting lumen (232) ensuring that no air bubbles remain within the fluid path.

Figure 20D:
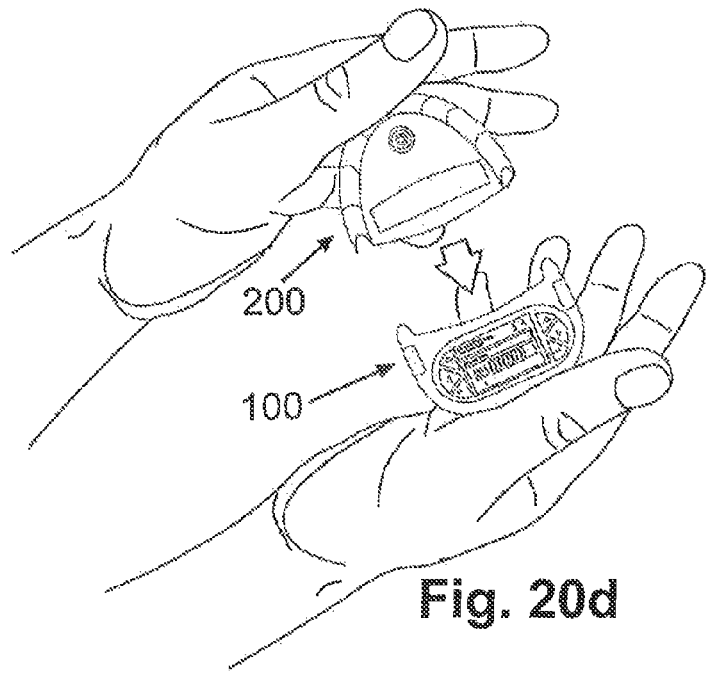
Figure 20G:
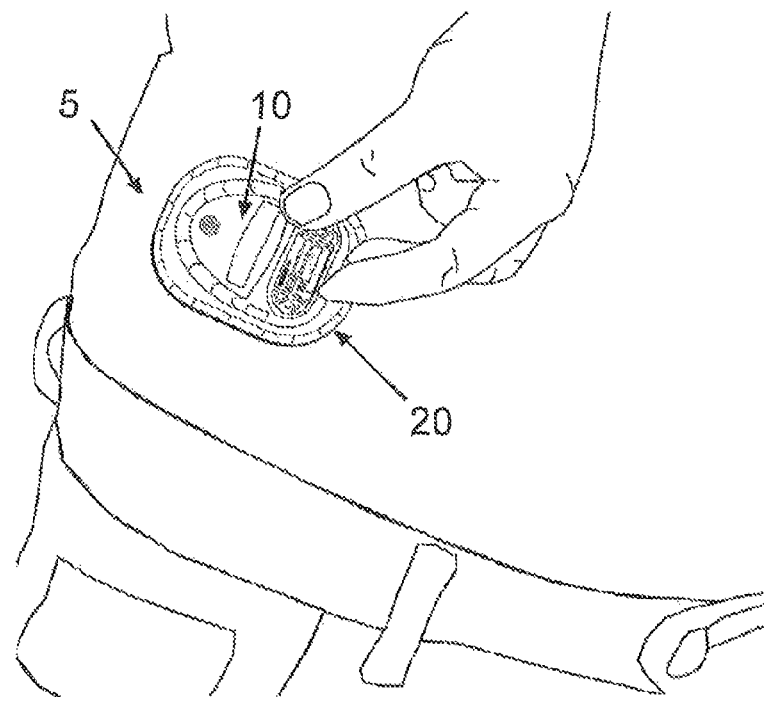
Figure 20H:
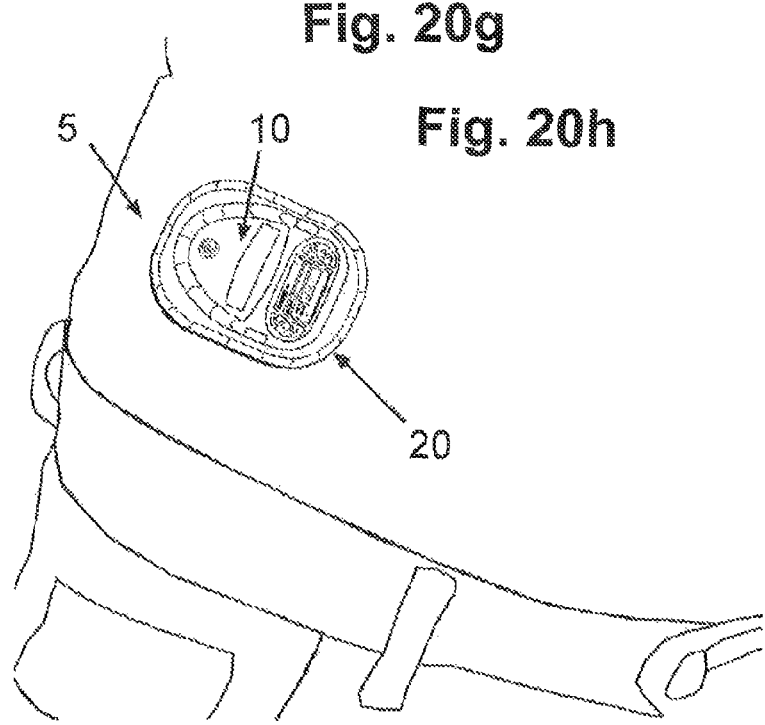

FIG. 20d shows pairing of the disposable part (200) and the reusable part (100). FIG. 20e shows the patch (10) setup (i.e. flow programming). FIG. 20f shows the cradle unit (20) adhered to the skin (5). FIG. 20g shows the patch (10) connection to the cradle unit (20). FIG. 20h shows the patch (10) connected to the cradle (20) on the user skin (5). FIG. 20i shows disconnection of the patch (10) from the cradle (20). In one implementation, the patch (10) is provided with a position sensor (not shown) which causes flow suspension upon patch (10) disconnection. FIG. 20j shows a user checking the patch (10) status. FIG. 20k shows the user programming the patch (10), for example inputting flow instructions. FIG. 20l shows reconnection of the patch (10) to the cradle (20). After connection the delivery can be resumed automatically as disclosed in our co-pending U.S. Provisional Application No. 60/963,045 filed on the Aug. 1, 2007, and titled "Detachable Portable Infusion Device", incorporated herein by reference in its entirety.

Figure 21A:
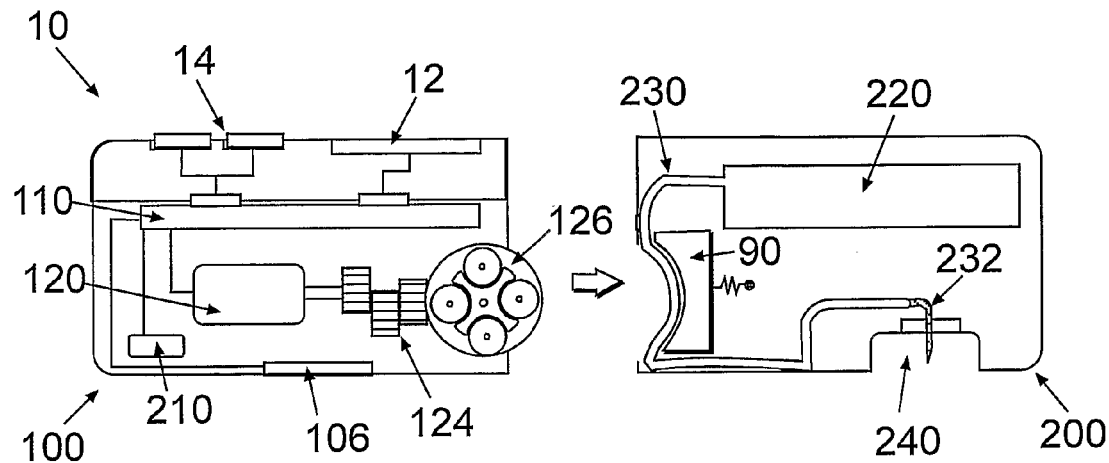
FIG. 21 shows one implementation of paring and connection of the two part patch unit employing a peristaltic mechanism.

FIG. 21a shows the reusable (100) and disposable (200) parts before connection. The reusable part (100) contains display (12), operating buttons (14), position sensor (106), processor (110), driving mechanism (120), battery (210), gear (124), and rotary wheel (126). The disposable part (200) includes a reservoir (220), delivery tube (230) connecting lumen (232), and an outlet port (240).

Figure 21B:
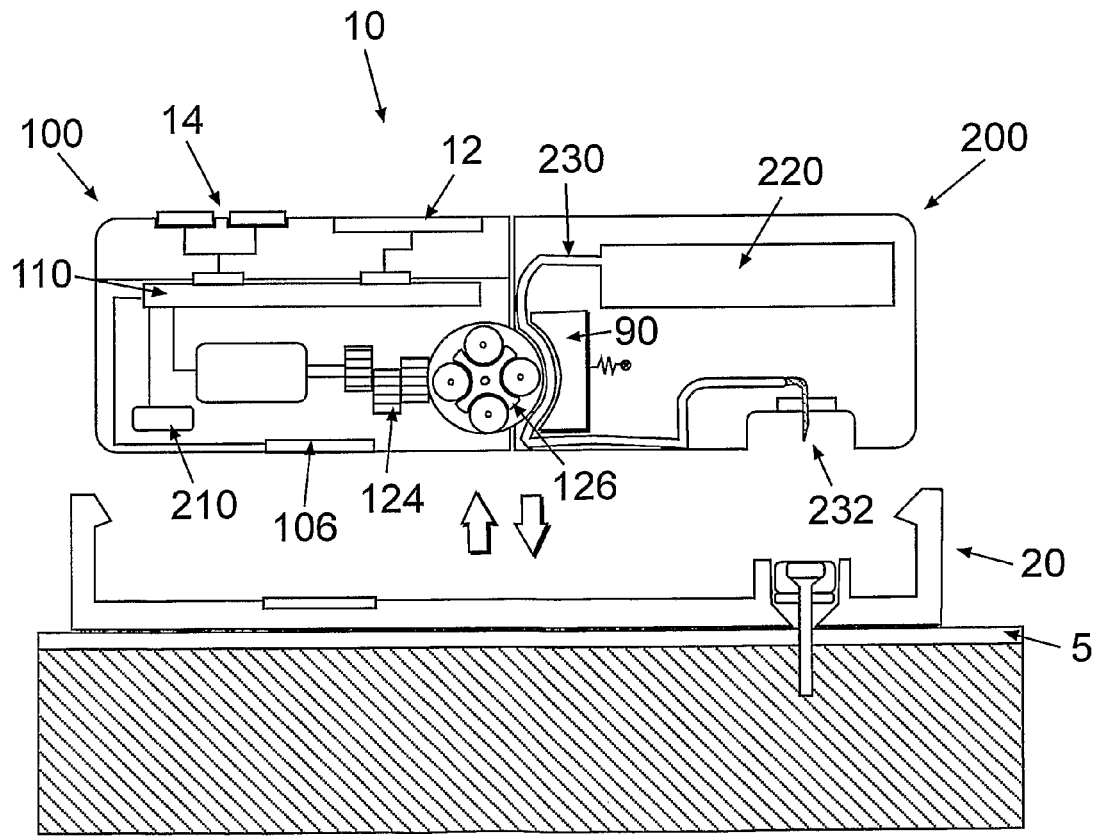

FIG. 21b shows the paired two part patch (10) which can be connected to and disconnected from the cradle unit (20). The rotary wheel (126) intends to periodically squeeze the delivery tube (230) and to positively displace fluid from the reservoir (220) to the connecting lumen (232).

Figure 21C:
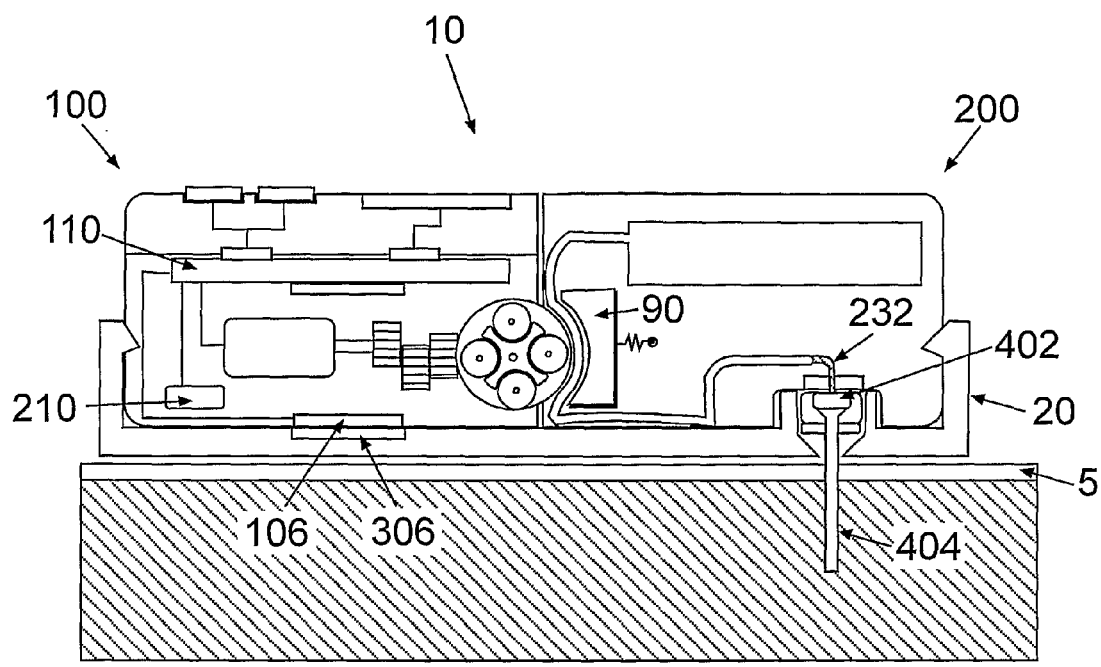

FIG. 21c shows the patch (10) connected to the cradle (20). The connecting lumen (232) pierces the septum (402) of the cannula (404). The two parts of the position sensor (106 and 306) are in close proximity notifying the processor (110) on a "connected position" and thus allowing fluid delivery.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Although a few variations have been described in detail above, other modifications are possible. For example, the logic flow depicted in the accompanying figures and described herein does not require the particular order shown, or sequential order, to achieve desirable results. Other implementations may be within the scope of the following claims.

Articles, patents, patent applications and other published and non-published documents provided above are herein incorporated by reference in their entirety.

What is claimed is:

1. A skin-adherable portable therapeutic fluid delivery device for delivering a therapeutic fluid into a body of a patient comprising:
    a cannula for delivering the therapeutic fluid into the body of the patient;
    a cradle unit configured for adhesively securing to the skin of the patient and defining an opening for providing a passageway for the cannula, the cradle unit comprising one or more anchors for securing a proximal end of the cannula to the cradle after insertion of the cannula into the body of the patient;
    a skin-adherable patch unit connectable to the cradle unit and to the cannula, the patch unit comprising a pump, a reservoir, a processor, a user interface and a display, wherein:
        the processor is configured for controlling the pump to deliver the therapeutic fluid from the reservoir to the body of the patient according to one or more inputs, the one or more inputs corresponding to at least one of a delivery rate and a delivery profile,
        the user interface is configured for adjusting the one or more inputs; and
        the display is operable for displaying patch information when the patch unit is disconnected from the delivery means, the patch information including at least one of the one or more inputs.

2. The device of claim 1, further comprising a cover for substantially covering the display.

3. The device of claim 1, wherein the display comprises a touch sensitive screen.

4. The device of claim 1, wherein the display is further configured for displaying one or more of: a bodily analyte level, nutrition values of foods, an amount of carbohydrates, an amount of therapeutic fluid held in the reservoir and at least one of amounts and percentages of delivered therapeutic fluid.

5. The device of claim 1, wherein the display comprises a liquid crystal display.

6. The device of claim 1, wherein the patch unit includes:
    a disposable part having the power source and the reservoir, and
    a reusable part having at least a portion of the pump, the processor, the user interface and the display,
    wherein the patch unit is operable upon connection of the reusable part and the disposable part.

7. The device of claim 6, wherein the disposable part and the reusable part are secured together either in a side by side configuration or a sandwich configuration.

8. The device of claim 1, wherein the patch unit is configured for operation by remote control.

9. The device of claim 1, wherein the patch unit is provided with at least one manual control switch for delivering the therapeutic fluid corresponding to the bolus profile.

10. The device of claim 1, wherein the pump of the patch unit includes a peristaltic mechanism or a piston for delivering the therapeutic fluid into the body of the patient.

11. The device of claim 1, wherein the therapeutic fluid comprises insulin.

12. The device of claim 1, wherein the device further includes a sensor for sensing a bodily analyte level.

13. The device of claim 12, wherein the bodily analyte comprises glucose.

14. The device of claim 1, wherein the cradle includes a well defining the opening for insertion of a cannula therein.

15. The device of claim 1, wherein the cradle unit comprises:
   a cradle base configured as a substantially flat sheet with an adhesive layer for adhering the cradle unit to the skin of the patient and having anchors for connection and disconnection of the patch unit thereto.

16. The device of claim 1, wherein the processor is configured for controlling the patch unit based on a position indication signal received from a position detector, wherein the signal corresponds to whether the patch unit is connected to or disconnected from the cradle unit.

17. The device of claim 1, wherein the processor is configured for programming upon disconnection of the patch unit from the cradle unit.

18. The device of claim 1, wherein the processor is configured to:
   receive the one or more inputs during disconnection from the cradle unit; and
   executing operation of the pump upon connection of the patch unit to the cradle unit.

19. The device of claim 18, wherein the processor is configured for notifying the patient upon execution of the corresponding operation of the pump.

20. The device of claim 1, wherein the operation of the pump corresponds to at least one of the one or more inputs.

21. The device of claim 1, wherein the user interface is configured to operate and control the patch unit.

22. The device of claim 1, wherein the user interface includes at least one of: buttons, switches, keys, a keypad, icons, graphical objects, voice command receiver and a touch sensitive screen including one or more of the preceding.

23. The device of claim 1, further comprising a cradle unit connectable to the patch unit, the cannula being arranged on the cradle unit such that the cradle unit is disconnected from the patch unit when the patch unit is disconnected from the cannula.

24. A method for delivering a therapeutic fluid into a body of a patient using a therapeutic fluid delivery device comprising:
   providing a cradle unit configured for adhesively securing to the skin of the patient and defining an opening for providing a passageway for a cannula, the cradle unit comprising one or more anchors for securing a proximal end of the cannula to the cradle after insertion of the cannula into the body of the patient;
   providing a patch unit securable to the cradle unit, the patch unit comprising a reservoir, a pump, a power source, a processor, a user interface and a display;
   receiving one or more inputs from the user interface, the one or more inputs corresponding to at least one of a basal rate and a bolus profile;
   displaying at least one of an indication of therapeutic fluid flow, a pump operation and the one or more inputs on a display of the patch unit; and
   controlling and/or operating the pump according to the one or more inputs.

25. The method of claim 24, wherein the patch unit further includes a cover for substantially covering the display.

26. The method of claim 24, wherein the display is touch sensitive.

27. The method of claim 24, wherein the patch unit includes:
   a disposable part having the power source and the reservoir, and
   a reusable part having at least a portion of the pump, the processor, the user interface and the display; and
   wherein control and/or operation of the pump is established upon coupling the reusable part and the disposable part.

28. The method of claim 24, wherein the cradle unit includes a well defining the opening for insertion of a cannula therein, a cradle base is configured as a substantially flat sheet with an adhesive layer for adhering the cradle unit to the skin of the patient and comprises one or more additional anchors for connection and disconnection of the patch unit to the cradle unit.

29. The method of claim 24, further comprising receiving an additional input comprising a level of a bodily analyte.

30. The method of claim 24, wherein the display is configured for operation upon the disconnection of the patch unit from the cradle unit and/or the skin of the patient.

31. The method of claim 24, further comprising displaying one or more of: a bodily analyte level, nutrition values of foods, an amount of carbohydrates, an amount of therapeutic fluid held in the reservoir and at least one of an amount and percentage of delivered therapeutic fluid.

32. The method of claim 24, wherein the display comprises a liquid crystal display.

33. The method of claim 24, further comprising controlling the patch unit based on a position indication signal received from a position detector, wherein the signal corresponds to whether the patch unit is connected to or disconnected from the cradle unit.

34. The method of claim 24, further comprising programming the processor when the patch unit is disconnected from the cradle unit.

35. The method of claim 24, further comprising:
   receiving the one or more inputs and suspending operation of the pump corresponding to the one or more inputs when the patch unit is disconnected from the cradle unit; and
   executing operation of the pump upon connection of the patch unit to the cradle unit.

36. The method of claim 35, further comprising notifying the patient upon execution of the corresponding operation of the pump.

37. The method of claim 24, wherein the user interface comprises one or more of: buttons, switches, keys, a keypad, icons, graphical objects, voice command receiver and touch sensitive screen having one or more of the preceding.

38. A method for controlling and/or operating a portable ambulatory, therapeutic fluid delivery device, the method comprising:
   providing a cradle unit configured for adhesively securing to the skin of the patient and defining an opening for providing a passageway for a cannula, the cradle unit comprising one or more anchors for securing a proximal end of the cannula to the cradle after insertion of the cannula into the body of the patient;
   providing a patch unit securable to the cradle unit, the patch unit comprising a reservoir, a pump, a power source, a processor, a user interface and a display;
   disconnecting the patch unit from the cradle or from the skin of the patient;

displaying on the display at least one of an indication of therapeutic fluid flow and operation of the pump when the patch unit is disconnected from the cradle unit and from the cannula;

connecting the patch unit to the cradle unit and the cannula for delivering the therapeutic fluid into the body.

39. The method of claim 38, further comprising programming the processor for controlling the patch unit by using the user interface when the patch unit is disconnected from the cradle unit or from the skin of the patient.

40. The method of claim 39, wherein upon connecting the patch unit, initiating therapeutic fluid delivery in accordance with the programming of the processor.

41. The method of claim 40, comprising notifying the user of initiating therapeutic fluid delivery.

42. The method of claim 41, wherein notifying the user comprises generating at least one of an audible or vibrational notification.

43. The method of claim 39, further comprising suspending fluid delivery when the patch unit is disconnected from at least one of the cradle unit and from the cannula.

44. The method of claim 39, wherein the display comprises a touch sensitive screen, and wherein the touch sensitive screen is used to program the processor.

45. The method of claim 38, wherein displaying further includes displaying one or more of: a bodily analyte level, nutrition values of foods, an amount of carbohydrates, an amount of therapeutic fluid held in the reservoir and at least one of an amount and percentage of delivered therapeutic fluid.

46. The device of claim 39, wherein the user interface comprises one or more of: buttons, switches, keys, a keypad, icons, graphical objects, voice command receiver and touch sensitive screen having one or more of the preceding.

47. The method of claim 38, wherein the device further comprises a cover for substantially covering the display.

48. The method of claim 38, wherein connecting the patch unit to at least one of the cradle unit and to the skin of the patient results in the display facing the cradle unit or the skin of the patient.

49. The method of claim 38, further comprising receiving an indication from a position sensor whether the patch unit is connected to or disconnected from the cradle unit or skin of the patient.

50. The method of claim 38, further comprising controlling the patch unit by using a remote control unit.

51. The method of claim 38, wherein the patch unit includes:

a disposable part having the power source and the reservoir, and a reusable part including at least a portion of the pump, the processor, the user interface and the display, and wherein coupling of the disposable part and reusable part allows operation of at least the display and user interface.

\* \* \* \* \*